United States Patent
Fremder et al.

(10) Patent No.: US 10,744,186 B2
(45) Date of Patent: Aug. 18, 2020

(54) METHOD OF TREATING CANCER WITH COMPOSITIONS COMPRISING IL-31

(71) Applicant: TECHNION RESEARCH & DEVELOPMENT FOUNDATION LIMITED, Haifa (IL)

(72) Inventors: Ella Fremder, Haifa (IL); Ami Aronheim, Binyamina (IL); Yuval Shaked, Binyamina (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/935,070

(22) Filed: Mar. 26, 2018

(65) Prior Publication Data

US 2018/0296644 A1 Oct. 18, 2018

Related U.S. Application Data

(62) Division of application No. 15/310,514, filed as application No. PCT/IL2015/050498 on May 12, 2015, now abandoned.

(60) Provisional application No. 61/991,641, filed on May 12, 2014.

(51) Int. Cl.
| | |
|---|---|
| *A61K 38/20* | (2006.01) |
| *C07K 14/54* | (2006.01) |
| *A61K 39/39* | (2006.01) |
| *A61K 39/00* | (2006.01) |
| *C12N 15/113* | (2010.01) |
| *A61K 9/127* | (2006.01) |

(52) U.S. Cl.
CPC ............ *A61K 38/20* (2013.01); *A61K 9/1273* (2013.01); *A61K 39/39* (2013.01); *C07K 14/54* (2013.01); *C12N 15/113* (2013.01); *C12N 15/1136* (2013.01); *A61K 2039/55527* (2013.01); *C07K 2319/30* (2013.01); *C07K 2319/33* (2013.01); *C07K 2319/50* (2013.01); *C12N 2310/14* (2013.01); *C12N 2310/531* (2013.01)

(58) Field of Classification Search
CPC ................................ A61K 38/20; C07K 14/54
See application file for complete search history.

(56) References Cited

U.S. PATENT DOCUMENTS

| 6,331,425 B1 | 12/2001 | Taylor et al. |
| 7,064,187 B2 | 6/2006 | Stone |
| 2006/0228329 A1 | 10/2006 | Brady et al. |

FOREIGN PATENT DOCUMENTS

| WO | WO-03060090 | 7/2003 |
| WO | WO-2006/081573 | 3/2007 |
| WO | WO-2008/086505 | 7/2008 |
| WO | WO-2012/178137 | 12/2012 |

OTHER PUBLICATIONS

Folkman J., Angiogenesis-dependent diseases, Semin. Oncol. 28, 536-542, 2001. (Year: 2001).*
Vazquez-Lombardi et al. "Molecular Engineering of Therapeutic Cytokines", Antibodies, Jul. 3, 2013, vol. 2, No. 3, pp. 426-451.
Pellequer et al. "Formulation of liposomes associated with recombinant interleukin-2: effect on interleukin-2 activity", Biomedicine and Pharmacotherapy. Apr. 1, 2004, vol. 58, No. 3, pp. 162-167.
Jazayeri et al. "Fc-based cytokines: Prospects for engineering superior therapeutics", BIOD, ADIS International Ltd, Jan. 1, 2008, vol. 22, No. 1, pp. 11-26.
K-M et al. "High level epression and secretion of Fc-X fusion proteins in mammalian cells", Protein Engineering, Oxford Uni. Press, Jun. 1, 1998, vol. 11, No. 6, pp. 495-500.
Zhang et al. "Structures and biological functions of IL-31 and IL-31 receptors", Cytokine and Growth Factor Reviews, Oct. 1, 2008, vol. 19, No. 5-6, pp. 347-356.
Le Saux et al. "Molecular dissection of human interleukin-31-mediated signal transduction through site-directed mutagenesis", Journal of Biological Chemistry, American Society for Biochemistry and Molecular Biology, Nov. 17, 2009. vol. 285, No. 5, pp. 3470-3477.
Guo et al. "Interleukin-6 signaling pathway in targeted therapy for cancer" Cancer treatment reviews, Nov. 1, 2012, vol. 38, No. 07, pp. 904-910.
Voronov et al. "The role IL-1 in tumor-mediated angiogeneis", Frontiers in Physiology, Mar. 28, 2014, vol. 5, pp. 1-11.
Office Action of U.S. Appl. No. 15/310,514 dated Dec. 28, 2017.
Puskas J et al. "Development of an attenuated interleukin-2 fusion protein that can be activated by tumour-expressed proteases" Immunology., 133(2):pp. 206-20. doi: 10.1111/j.1365-2567.2011.03428. x. Published Mar. 23, 2011.
Constantinou et al. Half-Life Extension with Pharmaceutical Formulations: Polysialic acid and polysialylation to modulate antibody pharmacokinetics, pp. 95-115, in Therapeutic proteins: strategies to modulate their plasma half-lives, edited by Roland Kontermann, John Wiley |& Sons, Inc. 2011.
U.S. Final Office Action for U.S. Appl. No. 15/310,514, dated May 30, 2018.

* cited by examiner

*Primary Examiner* — Elly-Gerald Stoica
(74) *Attorney, Agent, or Firm* — Pearl Cohen Zedek Latzer Baratz LLP

(57) ABSTRACT

A method for treating cancer and/or preventing or reducing metastasis or treating angiogenesis related disorders comprising the step of administering IL-31 or peptide which is at least about 70%, homologous to the IL-31 sequence as set forth in SEQ ID No. 1.

17 Claims, 23 Drawing Sheets

Specification includes a Sequence Listing.

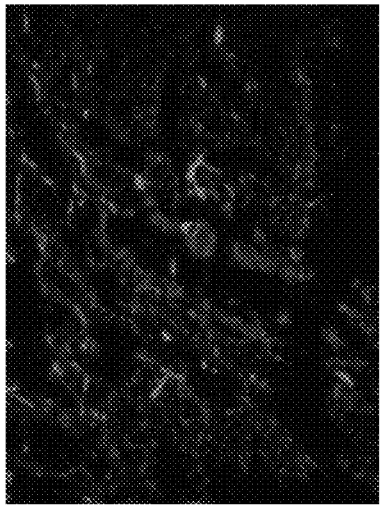
Fig. 3B

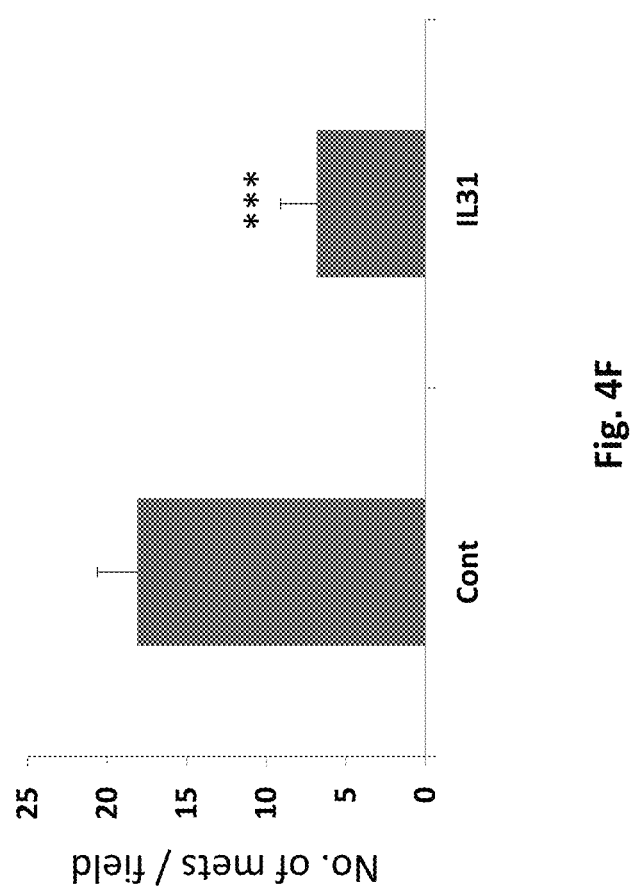

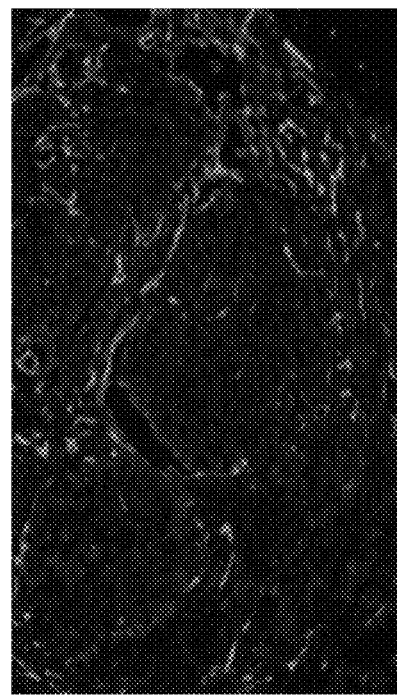
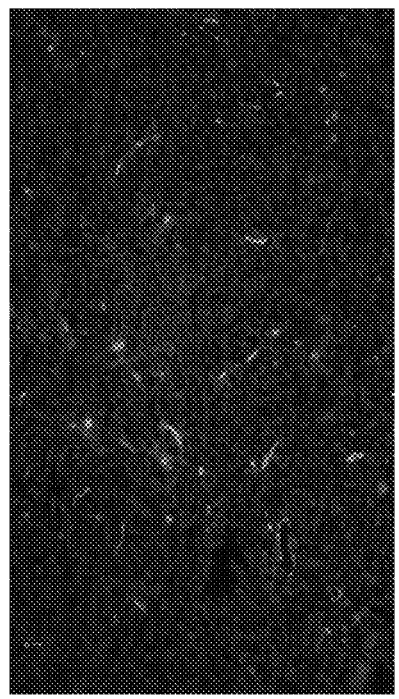
Fig. 4H

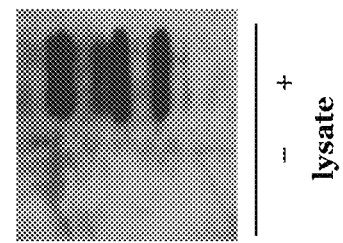
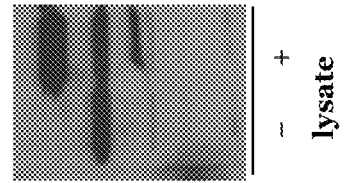
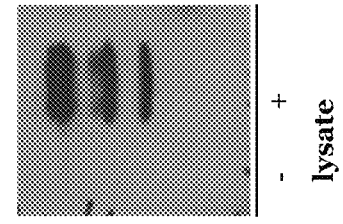
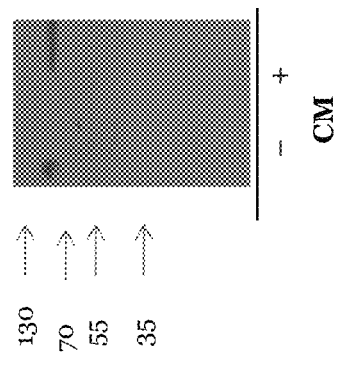
Fig. 8A

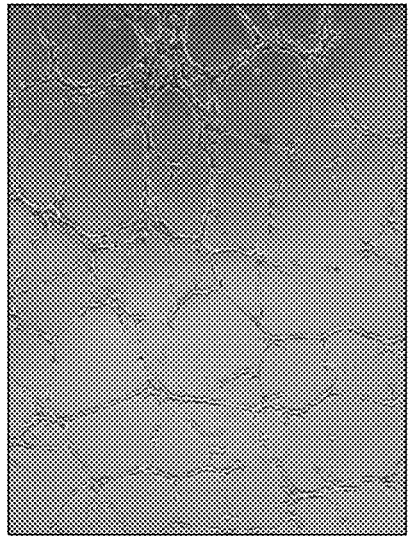
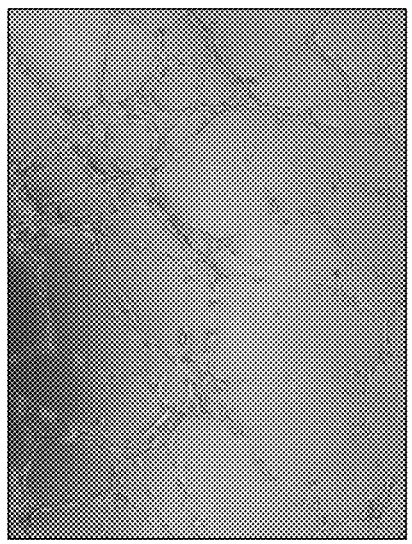
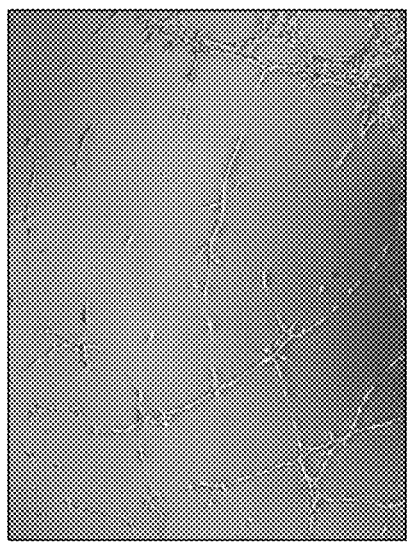
Fig. 9A

METHOD OF TREATING CANCER WITH COMPOSITIONS COMPRISING IL-31

CROSS-REFERENCE TO RELATED APPLICATIONS

This application is a Divisional of U.S. application Ser. No. 15/310,514, filed on Nov. 11, 2016, which is a National Phase Application of PCT International Application No. PCT/IL2015/050498, International Filing Date May 12, 2015, claiming the benefit of U.S. Patent Application No. 61/991,641, filed May 12, 2014, all of which are hereby incorporated by reference.

BACKGROUND OF THE INVENTION

Cancer is a leading cause of death in most countries, and the result of billions of dollars in healthcare expense around the world. It is now well established that a variety of cancers are caused, at least in part, by genetic abnormalities that result in either the overexpression of cancer causing genes, called "oncogenes," or from loss of function mutations in protective genes, often called "tumor suppressor" genes. One of the main obstacles in clinical oncology is that tumors can usually resist therapy, leading to tumor regrowth and even metastasis. There are many reasons that may explain why tumor cells become resistant to anti-cancer drugs, such as the ability of tumor cells to undergo selection for acquired resistance.

It has been demonstrated that several types of bone marrow derived cells home-in on chemotherapy-treated tumors and colonize there, leading to increased angiogenesis and metastasis.

The contribution of host cells to tumor growth is not solely dependent on angiogenesis. Recent studies indicated that immune cells, such as macrophages, also related to as tumor associated macrophages (TAMs) contribute to tumor growth. Macrophages are myeloid cells that are linked with inflammation. There are two main phenotypes of macrophages: M1 and M2. These two phenotypes are associated not only with tumors, but also with other pathological and physiological conditions related to the inflammatory cascade. During the inflammatory process M1 macrophages initially arrive and colonize the damaged tissue. They secrete various cytokines and chemokines at the inflammatory site, which ignite the inflammatory cascade. M1 macrophages have high phagocytotic properties and they secrete pro-inflammatory factors. On the other hand, M2 macrophages colonize the inflammatory tissue only a few days after M1 macrophages colonized the tissue. Their role is to stop the inflammatory process, and to initiate a regeneration process. Therefore, they secrete anti-inflammatory cytokines and growth factors known to repair damaged tissue, among those are factors promoting cell proliferation, migration, and activation. In cancer, M2 macrophages were found to substantially contribute to the tumorigenesis process and to metastasis, while M1 macrophages most likely contribute to the inhibition of pro-tumorigenic properties of cancer cells by creating an acute inflammatory process.

IL-31 is an immunoregulatory cytokine that is mainly produced by activated Th2 cells. IL-31 acts through the heterodimeric receptors of IL-31 (IL-31R) and oncostatin M receptor (OSMR), which are expressed on IL-31 activated monocytes and on epithelial cells.

The possible role of IL-31 as an anti-cancer compound was not investigated as of to date.

There is a need in identifying a new treatment for cancer.

SUMMARY OF THE INVENTION

This application is directed to a method for treating cancer and/or preventing or reducing metastasis comprising the step of administering IL-31, a fused protein comprising IL-31, an agent which up-regulates IL-31, an IL-31 receptor agonist or a complex comprising either IL-31 or a fused protein that comprises IL-31 to a subject in need, thereby treating cancer and/or reducing or preventing metastasis.

In one embodiment of the invention, the cancer is selected from the group consisting of brain cancer, oropharyngeal cancer, nasopharyngeal cancer, renal cancer, biliary cancer, prostatic cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head & neck cancer, prostate cancer, esophageal cancer, tracheal cancer, skin cancer, such as without being limited, melanoma or squamous cell carcinoma, brain cancer, such as without being limited, neuroblastoma, glioblastoma, astrositoma, liver cancer, bladder cancer, stomach cancer, pancreatic cancer, ovarian cancer, uterine cancer, cervical cancer, testicular cancer, colon cancer, rectal cancer or skin cancer. In some embodiments, the cancer is hematological malignancies, such as, multiple myeloma, acute lymphocytic leukemia (ALL), acute myeloid leukemia (AML), chronic lymphoblasic leukemia or chronic myeloid leukemia (CML). In some embodiments, the cancer is mesothieloma.

This application is further directed to a method for treating angiogenesis related disorder comprising the step of administering IL-31, a fused protein comprising IL-31, or a complex comprising either IL-31 or a fused protein that comprises IL-31 to a subject in need, thereby treating the angiogenesis related disorder.

In one embodiment of the invention, the related disorder is selected from the group consisting of cancer, arthritis, rheumatoid arthritis, atherosclerotic plaques, corneal graft neovascularization, hypertrophic or keloid scars, proliferative retinopathy, diabetic retinopathy, macular degeneration or age related macular degeneration (AMD), granulation, neovascular glaucoma and uveitis. In some embodiments, the angiogenesis related disorder is "fibrosis-related diseases, e.g., liver fibrosis and lung fibrosis. In some embodiments, the angiogenesis related disorder is asthma.

This application is further directed to a fused protein comprising IL-31. In some embodiments, the IL-31 is attached to a heterologous amino acid sequence. In some embodiments, the heterologous amino acid sequence comprises an immunoglobulin amino acid sequence. In some embodiments, the immunoglobulin amino acid sequence comprises IgG.

In one embodiment of the invention, the fused protein further comprises IgG.

In one embodiment of the invention, the fused protein further comprises a cleavage site for an enzyme.

In one embodiment of the invention, the enzyme is trypsin, PSA, MMP-9/2 or cathepsin or any combination thereof.

This application is further directed to a nucleic acid encoding a fused protein comprising IL-31.

In one embodiment of the invention, the nucleic acid further comprises a nucleic acid encoding IgG.

In one embodiment of the invention, the nucleic acid further comprises a nucleic acid encoding a cleavage site for enzymes.

In one embodiment of the invention, the enzyme is trypsin, PSA, MMP-9/2 or cathepsin or any combination thereof.

This application is further directed to a vector comprising the nucleic acid of any one of the previous embodiments.

This application is further directed to a cell transformed with a vector comprising the nucleic acid of any one of the previous embodiments.

This application is further directed to a complex comprising IL-31 or a fused protein comprising IL-3 and non-proteinaceous or proteinaceous moiety.

In one embodiment of the invention, the non-proteinaceous is polyethylene glycol (PEG) or derivative thereof, polyvinyl pyrrolidone (PVP), albumin, divinyl ether, maleic anhydride copolymer (DIVEMA; and poly(styrene comaleic anhydride) (SMA), hyaluronic acid (HA), alginic acid (AA), polyhydroxyethyl methacrylate (Poly-HEMA), glyme or polyisopropylacrylamide or any combination thereof.

In one embodiment of the invention the complex is in a form of a liposome or a micelle.

In some embodiments of the invention, there is provided an IL-31 protein or peptide which is at least about 70%, homologous to the IL-31 sequence as set forth in SEQ ID No. 1, a fused protein comprising IL-31 or peptide which is at least about 70% homologous to the IL-31 sequence as set forth in SEQ ID No. 1, an agent which up-regulates IL-31, an IL-31 receptor agonist or a complex comprising either IL-31 or peptide which is at least about 70%, homologous to the IL-31 sequence as set forth in SEQ ID No. 1 or a fused protein that comprises IL-31 or peptide which is at least about 70%, homologous to the IL-31 sequence as set forth in SEQ ID No. 1 for use in treating cancer and/or preventing or reducing metastasis.

In some embodiments, there is provided an IL-31 protein or peptide which is at least about 70%, homologous to the IL-31 sequence as set forth in SEQ ID No. 1, a fused protein comprising IL-31 or peptide which is at least about 70%, homologous to the IL-31 sequence as set forth in SEQ ID No. 1, an agent which up-regulates IL-31, an IL-31 receptor agonist or a complex comprising either IL-31 or peptide which is at least about 70%, homologous to the IL-31 sequence as set forth in SEQ ID No. 1 or a fused protein that comprises IL-31 or a peptide which is at least about 70%, homologous to the IL-31 sequence as set forth in SEQ ID No. 1 for use in treating angiogenesis related disorders.

In some embodiments of the invention, there is provided a method for treating cancer and/or preventing or reducing metastasis comprising the step of administering IL-31 or peptide which is at least about 70%, homologous to the IL-31 sequence as set forth in SEQ ID No. 1, a fused protein comprising IL-31 or peptide which is at least about 70%, homologous to the IL-31 sequence as set forth in SEQ ID No. 1, an agent which up-regulates IL-31, an IL-31 receptor agonist or a complex comprising either IL-31 or peptide which is at least about 70%, homologous to the IL-31 sequence as set forth in SEQ ID No. 1 or a fused protein that comprises IL-31 or peptide which is at least about 70%, homologous to the IL-31 sequence as set forth in SEQ ID No. 1, to a subject in need, thereby treating cancer and/or reducing or preventing metastasis.

In some embodiments of the invention, there is provided a method for treating angiogenesis related disorder comprising the step of administering IL-31 or peptide which is at least about 70%, homologous to the IL-31 sequence as set forth in SEQ ID No. 1, a fused protein comprising IL-31 or peptide which is at least about 70%, homologous to the IL-31 sequence as set forth in SEQ ID No. 1, an agent which up-regulates IL-31, an IL-31 receptor agonist or a complex comprising either IL-31 or peptide which is at least about 70%, homologous to the IL-31 sequence as set forth in SEQ ID No. 1 or a fused protein that comprises IL-31 or peptide which is at least about 70%, homologous to the IL-31 sequence as set forth in SEQ ID No. 1 to a subject in need, thereby treating the angiogenesis related disorder.

In some embodiments of the invention, there is provided a fused protein comprising IL-31 or peptide which is at least about 70%, homologous to the IL-31 sequence as set forth in SEQ ID No. 1.

In some embodiments of the invention, there is provided an IL-31 protein or peptide which is at least about 70%, homologous to the IL-31 sequence as set forth in SEQ ID No. 1 is attached to a heterologous amino acid sequence.

In some embodiments, the heterologous amino acid sequence comprises an immunoglobulin amino acid sequence, which may be IgG.

In some embodiments of the invention, there is provided a nucleic acid encoding a fused protein comprising IL-31 or peptide which is at least about 70%, homologous to the IL-31 sequence as set forth in SEQ ID No. 1.

In some embodiments, the nucleic acid encodes IgG.

The fused protein may further comprise a nucleic acid encoding a cleavage site for enzymes, wherein the enzyme may be trypsin, PSA, MMP-9/2 or cathepsin or any combination thereof.

In some embodiments, there is provided a complex comprising IL-31 or a fused protein comprising IL-31 or peptide which is at least about 70%, homologous to the IL-31 sequence as set forth in SEQ ID No. 1 and non-proteinaceous or proteinaceous moiety. The non proteinaceous may be polyethylene glycol (PEG) or derivative thereof, polyvinyl pyrrolidone (PVP), divinyl ether, albumin, maleic anhydride copolymer (DIVEMA), polysialic acid (PSA), poly (styrene comaleic anhydride) (SMA), hyaluronic acid (HA), alginic acid (AA), polyhydroxyethyl methacrylate (Poly-HEMA), glyme or polyisopropylacrylamide or any combination thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 2 (A and B)

FIGS. 3 (A-D): FIG. 3B presents microvessel density (MVD) and large vessel structures in tumor removed from mice injected with MC38 cells transfected with shIL-31 or scrambled plasmids; the number of vessel structures or cell per field were counted and plotted.

FIGS. 4 (A-I) FIGS. 4E and 4F compare the number of lung metastatic lesions using H&E staining of lung sections in tumors from mice implanted with 4T1 cells and infused with either rIL-31 or PBS (control)(FIG. 4E); Arrows represent the metastatic lesions in the lung section. The quantification of the number of metastatic lesions per field is provided (FIG. 4F).

FIGS. 4H and 4I, the tumors presented in FIG. 4G were removed at the end point, after the mice were treated with hIL-31-IgG for two weeks either by pump or by IP injections. (FIG. 4H) Tumors were sectioned and stained for CD31 (an endothelial cell marker). (FIG. 4I) Quantification of the number of vessels (MVD) per field is provided.

FIGS. 5 (A-C)

(FIG. 8G) 30 µg mIL31-IgG Vs. 200 µg mIL31. (FIG. 8H) 30 µg hIL31-IgG Vs. 200 µg hIL31.

DETAILED DESCRIPTION OF THE INVENTION

Figure 1A:
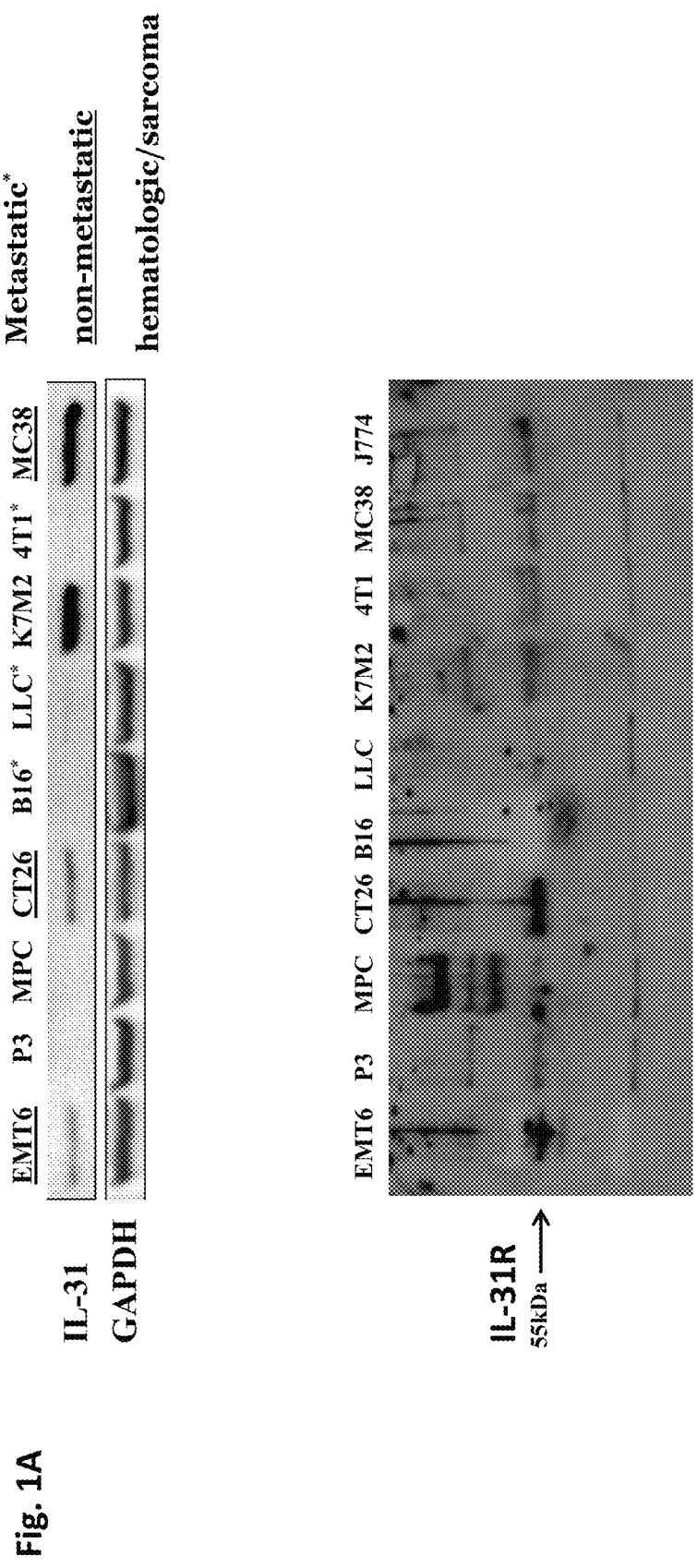
FIGS. 1(A-G): The upper image of FIG. 1A is a western blot image showing the expression level of IL-31 in various tumor cell lines and macrophages. Below is a western blot image showing the level of IL-31 receptor (IL-31R) in various tumor cell lines and macrophages. A star (*) represents metastatic cells. An underlined cell type represents a non-metastatic cell, other cell lines are hematologic cell lines. An inverse correlation between the expression of IL-31 and its receptor and the metastatic properties of tumor cells can be seen.
FIGS. 1B 1C, 1D and 1E present the viability of MC38 cells (FIG. 1B), 4T1 cells (FIG. 1C), CT26 cells (FIG. 1D) and HCT116 cells (FIG. 1E), respectively, in the presence of escalating doses of recombinant IL-31 (rIL-31) using Alamar-Blue assay.
FIGS. 1F and 1G present the number of cells of MC38 (FIG. 1F) and 4T1 (FIG. 1G) in the presence of different doses of rIL-31 using trypan blue to exclude dead cells.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

As shown in the Examples section, IL-31 was found to be highly effective in inhibiting tumor cells proliferation, tumor size and metastasis in cells and tumors. In an embodiment of the invention, the benefit of IL-31 in tumors may be dependent on the presence of IL-31 or IL-31R expression in the tumor. In some embodiments of the invention, as exemplified in Examples 2 and 4, IL-31 may have an indirect effect on any tumor cell, for example, via an effect on supporting cells in the tumor microenvironment i.e., endothelial cells and macrophages In some embodiments of the invention, there is provided a method for treating cancer comprising the step of administering IL-31, a fused protein comprising IL-31, or a complex comprising either IL-31 or a fused protein that comprises IL-31 to a subject in need, thereby treating cancer.

In some embodiments of the invention, there is provided a method for treating cancer comprising the step of contacting cancerous cells of the subject with a therapeutically effective amount of IL-31, a fused protein comprising IL-31, or a complex comprising either IL-31 or a fused protein that comprises IL-31, thereby treating the cancer.

In some embodiments of the invention, there is provided a method for treating cancer comprising the step of contacting cancerous cells of the subject with a therapeutically effective amount of an agent capable of up-regulating IL-31 or an agent that is an agonist to IL-31 receptors, thereby treating the cancer.

According to some embodiments of the invention, the contacting is effected in-vivo.

According to some embodiments of the invention, the contacting is effected ex-vivo.

In some embodiments of the invention, the cancer is an oral cancer, oropharyngeal cancer, nasopharyngeal cancer, respiratory cancer, a urogenital cancer, a gastrointestinal cancer, a central or peripheral nervous system tissue cancer, an endocrine or neuroendocrine cancer or a hematopoietic cancer.

According to some embodiments of the invention, the cancer is a glioma, a sarcoma, a carcinoma, a lymphoma, a melanoma, a fibroma, or a meningioma.

According to some embodiments of the invention, the cancer is brain cancer, oropharyngeal cancer, nasopharyngeal cancer, renal cancer, biliary cancer, prostatic cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer.

In some embodiments of the invention, the cancer is a breast cancer, a pancreatic cancer or a lung cancer.

In some embodiments of the invention, there is provided a method of preventing or reducing metastasis comprising the step of administering a therapeutically effective amount of IL-31, a fused protein comprising IL-31, an agent the up-regulates IL-31 or an agent that is an agonist to IL-31 receptor or a complex comprising either IL-31 or a fused protein that comprises IL-31, to a subject in need thereby preventing metastasis.

As used herein the term "treating cancer" refers to preventing, curing, reversing, attenuating, alleviating, minimizing or suppressing the cancer, as well as resulting in one or more of the following parameters: reduction in tumor size or burden, blocking of tumor growth, shifting the phenotype of the macrophage from M2 to M1, reduction in tumor-associated pain, long-term non-progression, induction of remission, reduction of metastasis, or increased patient survival.

As used herein the term "cancer" refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Typically, the cancer cells are in the form of a tumor; existing locally within an animal, or circulating in the blood stream as independent cells, for example, leukemic cells.

The method may further comprise administering a second anti-cancer therapy or a third anti-cancer therapy to the treated subject. The second and third anti-cancer therapies may be one or two or more of chemotherapy, radiotherapy, hormonal therapy, cytokine therapy, immunotherapy, targeted therapy, e.g., bortezomib, sunitinib, Herceptin, sorafenib and/or surgery. The second and third anti-cancer therapy may be administered to the subject prior to or after the IL-31 treatment or concurrent with the IL-31 treatment. As used herein, the IL-31 treatment includes treatments using IL-31, a fused protein comprising the same, IL-31 receptor agonist or an agent which up-regulates IL-31 or a complex comprising IL-31 or a fused protein thereof.

In some embodiments, the method of treatment may further comprise assessing the efficacy of the treatment by performing a PET scan on said subject or measuring the level of the relevant bio-markers.

In some embodiments of the invention, there is provided a method for treating angiogenesis related disorders or diseases comprising the step of administering a therapeutically effective amount of IL-31, a fused protein comprising IL-31, or a complex comprising either IL-31 or a fused protein that comprises IL-31 or an agent capable of upregulating IL-31 to a subject in need thereby treating an angiogenesis related disorder or disease.

As used herein the term "treating angiogenesis relate disorders" refers to preventing, curing, reversing, attenuating, alleviating, minimizing or suppressing the angiogenesis related disorders, as well as resulting in a decrease of abnormal or pathological angiogenesis or increased efficacy of functional angiogenesis by inhibiting permeabilization and thus increased patient survival or reduce symptoms. The method may further comprise administering an additional therapy prior to or after the IL-31 treatment or concurrent with the IL-31 treatment to the treated subject, such as, hormonal therapy, another anti-angiogenesis therapy, immunotherapy or a targeted therapy to the abnormal angiogenesis related disease.

According to some embodiments of the invention, the disease associated with angiogenesis is selected from the group consisting of cancer, arthritis, rheumatoid arthritis, atherosclerotic plaques, corneal graft neovascularization, hypertrophic or keloid scars, proliferative retinopathy, diabetic retinopathy, macular degeneration or age related macular degeneration (AMD), granulation, neovascular glaucoma and uveitis. In some embodiments, the angiogenesis related disorder is "fibrosis-related diseases, e.g., liver fibrosis and lung fibrosis. In some embodiments, the angiogenesis related disorder is asthma. In some embodiments, the angiogenesis related disorder is Idiopathic Pulmonary Fibrosis (IPF) and Myelofibrosis, Primary Sclerosing Cholangitis.

In some embodiments of the invention, angiogenesis-related diseases include, but are not limited to, inflammatory, autoimmune, and infectious diseases; angiogenesis-dependent cancer, including, for example, solid tumors, blood-borne tumors such as leukemias, and tumor metastases; benign tumors, for example hemangiomas, acoustic neuromas, neurofibromas, trachomas, and pyogenic granulomas; psoriasis; eczema; ocular angiogenic diseases, for example, diabetic retinopathy, retinopathy of prematurity, corneal graft rejection, retrolental fibroplasia, rubeosis; Osler-Webber Syndrome; myocardial angiogenesis; plaque neovascularization; telangiectasia; hemophiliac joints; angiofibroma; and wound granulation.

In addition, compositions comprising the active ingredient as defined herein can be used to treat diseases such as, but not limited to, intestinal adhesions, atherosclerosis, scleroderma, warts, and hypertrophic scars (i.e., keloids). Compositions of this invention may also be useful in the treatment of diseases that have angiogenesis as a pathologic consequence, such as cat scratch disease (Rochele minalia quintosa), ulcers (*Helobacter pylori*), tuberculosis, and leprosy. In some embodiments, the compositions which include the active ingredient of the invention may be used to treat inflammation or inflammation related disorders.

For example, human IL-31 (SEQ ID NO: 1 below) (Gene ID: 386653) is encoded by the following nucleic acid sequence:

(SEQ ID NO: 2)
ATGGCCTCTCACTCAGGCCCCTCGACGTCTGTGCTCTTTCTGTTCTGCTG

CCTGGGAGGCTGGCTGGCCTCCCACACGTTGCCCGTCCGTTTACTACGAC

CAAGTGATGATGTACAGAAAATAGTCGAGGAATTACAGTCCCTCTCGAAG

ATGCTTTTGAAAGATGTGGAGGAAGAGAAGGGCGTGCTCGTGTCCCAGAA

TTACACGCTGCCGTGTCTCAGCCCTGACGCCCAGCCGCCAAACAACATCC

ACAGCCCAGCCATCCGGGCATATCTCAAGACAATCAGACAGCTAGACAAC

AAATCTGTTATTGATGAGATCATAGAGCACCTCGACAAACTCATATTTCA

AGATGCACCAGAAACAAACATTTCTGTGCCAACAGACACCCATGAATGTA

AACGCTTCATCCTGACTATTTCTCAACAGTTTTCAGAGTGCATGGACCTC

GCACTAAAATCATTGACCTCTGGAGCCCAACAGGCCACCACTTAA.

Human IL-31 Amino Acid Sequence:

(SEQ ID NO: 1)
MASHSGPSTSVLFLFCCLGGWLASHTLPVRLLRPSDDVQKIVEELQSLSK

MLLKDVEEEKGVLVSQNYTLPCLSPDAQPPNNIHSPAIRAYLKTIRQLDN

KSVIDEIIEHLDKLIFQDAPETNISVPTDTHECKRFILTISQQFSECMDL

ALKSLTSGAQQATT (1-23: Signal peptide; 24-164: IL-31)

For example, mouse (*Mus musculus*) IL-31 (SEQ ID NO: 6 below) (Gene ID: 76399) is encoded by the following nucleic acid sequence:

(SEQ ID NO: 3)
ATGATCTTCCACACAGGAACAACGAAGCCTACCCTGGTGCTGCTTTGCTG

TATAGGAACCTGGCTGGCCACCTGCAGCTTGTCCTTCGGTGCCCCAATAT

CGAAGGAAGACTTAAGAACTACAATTGACCTCTTGAAACAAGAGTCTCAG

GATCTTTATAACAACTATAGCATAAAGCAGGCATCTGGGATGTCAGCAGA

-continued
CGAATCAATACAGCTGCCGTGTTTCAGCCTGGACCGGGAAGCATTAACCA

ACATCTCGGTCATCATAGCACATCTGGAGAAAGTCAAAGTGTTGAGCGAG

AACACAGTAGATACTTCTTGGGTGATAAGATGGCTAACAAACATCAGCTG

TTTCAACCCACTGAATTTAAACATTTCTGTGCCTGGAAATACTGATGAAT

CCTATGATTGTAAAGTGTTCGTGCTTACGGTTTTAAAGCAGTTCTCAAAC

TGCATGGCAGAACTGCAGGCTAAGGACAATACTACATGCTGA.

Mouse IL-31 Amino Acid Sequence:

(SEQ ID NO: 6)
MIFHTGTTKPTLVLLCCIGTWLATCSLSFGAPISKEDLRTTIDLLKQESQ

DLYNNYSIKQASGMSADESIQLPCFSLDREALTNISVIIAHLEKVKVLSE

NTVDTSWVIRWLTNISCFNPLNLNISVPGNTDESYDCKVFVLTVLKQFSN

CMAELQAKDNTTC (1-23: Signal peptide; 24-163: IL-31)

Specifically, IL-31 SEQ ID. No. 1 (Gene ID. No. 386653 (for human), Gene ID. No 76399 (for *Mus Musculus*), Gene ID. No 744097 (for *Pan Troglodytes* (chimpanzee)), Gene ID. No. 102179123 (for *Capra Hircus* (goat)), which form a part of the invention also refers to homologs (e.g., polypeptides), which are at least about 50%, at least about 55%, at least about 60%, at least about 65%, at least about 70%, at least about 75%, at least about 80%, at least about 85%, at least about 87%, at least about 89%, at least about 91%, at least about 93%, at least about 95%, at least about 97% or more, homologous to the IL-31 sequence as set forth in SEQ ID No. 1 listed herein, as determined using any appropriate means, including BlastP software of the National Center of Biotechnology Information (NCBI) using default parameters). The homolog may also refer to a deletion, insertion, or substitution variant, including an amino acid substitution, thereof and biologically active polypeptide fragments thereof.

As used herein the term "about" refers to ±10%.

As used herein a "pharmaceutical composition" refers to a preparation of one or more of the active ingredients described herein with other chemical components such as physiologically or pharmaceutically suitable carriers and excipients. The purpose of a pharmaceutical composition is to facilitate administration of a compound to an organism.

Herein the term "active ingredient" refers to IL-31 or a fused protein comprising IL-31 or to a complex comprising the IL-31 or the fused protein comprising IL-31, or to the agent capable of up-regulating IL-31, or an IL-31 receptor agonist any one of which is accountable for biological effect as described herein. Further included are constructs which include nucleic acid encoding the same.

Hereinafter, the phrases "physiologically acceptable carrier" and "pharmaceutically acceptable carrier", which may be interchangeably used, refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

In some embodiments, the invention further envisages inclusion of the IL-31 sequence or a fused protein thereof in a complex where it is attached to proteinaceous (e.g., heterologous amino acid sequence) or non-proteinaceous moieties (e.g., PEG), each of which being capable of prolonging the half-life of the composition while in circulation.

Such a molecule is highly stable (resistant to in-vivo proteaolytic activity, probably due to steric hindrance conferred by the non-proteinaceous moiety) and may be produced using common solid phase synthesis. Further recombinant techniques may still be used, whereby the recombinant peptide product is subjected to in-vitro modification (e.g., PEGylation as further described herein below).

The phrase "non-proteinaceous moiety" as used herein refers to a molecule not including peptide bonded amino acids that is attached to the above-described IL-31 amino acid sequence. According to some embodiments the non-proteinaceous moiety may be a polymer or a co-polymer (synthetic or natural). Non-limiting examples of the non-proteinaceous moiety of the present invention include polyethylene glycol (PEG) or derivative thereof, Polyvinyl pyrrolidone (PVP), albumin, divinyl ether and maleic anhydride copolymer (DIVEMA); polysialic acid (PSA) and/or poly (styrene comaleic anhydride) (SMA). Additionally, complexes which can protect IL-31 from the environment and thus keep its stability may be used, including, for example, liposomes or micelles containing IL-31, IL-31 receptor agonist, an agent that up-regulates IL-31 or a fused protein comprising thereof are also included in the invention.

By "an agent that is an agonist to IL-31 receptors" or IL-31 receptor agonist" it is meant any agent that binds to an IL-31 receptor and produce a biological response as defined herein. Such an agent may be a protein, a small molecule, an antibody and the like.

According to some embodiments of the invention, the IL-31 or the fused protein comprising IL-31 of the invention is attached to a non-proteinaceous moiety, which may act as a sustained-release enhancing agent. Exemplary sustained-release enhancing agents include, but are not limited to hyaluronic acid (HA), alginic acid (AA), polyhydroxyethyl methacrylate (Poly-HEMA), glyme and polyisopropylacrylamide.

Attaching the amino acid sequence component of the IL-31 or the fused protein comprising thereof of the invention to other non-amino acid agents may be by covalent linking or by non-covalent complexion, for example, by complexion to a hydrophobic polymer, which can be degraded or cleaved producing a compound capable of sustained release; by entrapping the amino acid part of the IL-31 or the fused protein comprising thereof in liposomes or micelles to produce a complex comprising the IL-31 or the fused protein comprising the same. The association may be by the entrapment of the amino acid sequence within the other component (liposome, micelle) or the impregnation of the amino acid sequence within a polymer to produce the final peptide of the invention.

In some embodiments, the PEG derivative is N-hydroxysuccinimide (NHS) esters of PEG carboxylic acids, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. PEG-maleimide, PEG-vinylsulfone (VS), PEG-acrylate (AC) or PEG-orthopyridyl disulfide may be also used.

The non-proteinaceous moiety may be attached to the IL-31 amino acid sequence in any chosen position, provided that the therapeutic activity of IL-31 is retained.

In some embodiments, the conjugated IL-31 molecules are separated, purified and qualified using e.g., high-performance liquid chromatography (HPLC).

Molecules of this aspect of the present invention may be biochemically synthesized such as by using standard solid phase techniques. These methods include exclusive solid phase synthesis, partial solid phase synthesis methods, fragment condensation and classical solution synthesis.

Solid phase peptide synthesis procedures are well known in the art and further described by John Morrow Stewart and Janis Dillaha Young, Solid Phase Peptide Syntheses (2nd Ed., Pierce Chemical Company, 1984).

In instances where large amounts of the peptides of the present invention are desired, they may be produced using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988&, Methods for Plant Molecular Biology, Academic Press, NY, Section VIII, pp 421-463.

In some embodiments of the invention, there is provided a fused protein that comprises IL-31 as defined herein together with one or more molecule which extend the half life of IL-31 in the plasma. In some embodiments, the fused protein further comprises a linker. In some embodiments of the invention, there is provided a fused protein that comprises IL-31 and a protein that stabilizes IL-31 or protect it in the blood stream or at the tissue. In some embodiments the fused protein comprises IL-31 attached to a heterologous amino acid sequence. In some embodiments, the heterologous amino acid sequence comprises an immunoglobulin amino acid sequence.

In some embodiments of the invention, there is provided a fused protein that comprises IL-31 and IgG. The IgG may any subclasses or isotypes thereof, e.g., IgG1, IgG2, IgG3, IgG4. For example:

*Mus musculus* Immunoglobulin Gamma Heavy Chain (Partial Cds of DQ381548)

```
                                                  (SEQ ID NO: 4)
GTGCCCAGGGATTGTGGTTGTAAGCCTTGCATATGTACAGTCCCAGAAGT

ATCATCTGTCTTCATCTTCCCCCCAAAGCCCAAGGATGTGCTCACCATTA

CTCTGACTCCTAAGGTCACGTGTGTTGTGGTAGACATCAGCAAGGATGAT

CCCGAGGTCCAGTTCAGCTGGTTTGTAGATGATGTGGAGGTGCACACAGC

TCAGACGCAACCCCGGGAGGAGCAGTTCAACAGCACTTTCCGCTCAGTCA

GTGAACTTCCCATCATGCACCAGGACTGGCTCAATGGCAAGGAGTTCAAA

TGCAGGGTCAACAGTGCAGCTTTCCCTGCCCCCATCGAGAAAACCATCTC

CAAAACCAAAGGCAGACCGAAGGCTCCACAGGTGTACACCATTCCACCTC

CCAAGGAGCAGATGGCCAAGGATAAAGTCAGTCTGACCTGCATGATAACA

GACTTCTTCCCTGAAGACATTACTGTGGAGTGGCAGTGGAATGGGCAGCC
```

-continued
AGCGGAGAACTACAAGAACACTCAGCCCATCATGGACACAGATGGCTCTT

ACTTCGTCTACAGCAAGCTCAATGTGCAGAAGAGCAACTGGGAGGCAGGA

AATACTTTCACCTGCTCTGTGTTACATGAGGGCCTGCACAACCACCATAC

TGAGAAGAGCCTCTCCCACTCTCCTGGTAAA.

*Homo sapiens* mRNA for IgG H Chain, (Partial Cds of AB776838)

(SEQ ID NO: 5)
GAGCCCAAATCTTGTGACAAAACTCACACATGCCCACCGTGCCCAGCACC

TGAACTCCTGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGAGGAGATGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCGGGTAAA.

In some embodiments, the term "antibody" refers to the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, $C_L$, Fab and Fc fragments.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

In some embodiments, a construct which includes a nucleic acid sequence for IL-31 as defined herein, for example, SEQ ID. No. 2, and a nucleic acid sequence for IgG for example, SEQ ID. No. 5 may be used in the construct. In some embodiments of the invention, the IL-31 and the IgG are directly fused to each other.

Serum albumin can also be engaged in half-life extension through modules with the capacity to non-covalently interact with albumin. In these approaches, an albumin-binding moiety is either conjugated or genetically fused to the therapeutic protein Proteins with albumin-binding activity are known from certain bacteria. For example, streptococcal protein G contains several small albumin-binding domains (ABD) composed of roughly 50 amino acid residues (6 kDa). Fusion of an ABD to a protein results in a strongly extended half-life (see Roland E Kontermann, trategies for extended serum half-life of protein therapeutics, Current Opinion in Biotechnology 2011, 22:868-876.

In some embodiments of the invention, the IL-31 and the IgG and/or any other protein that may be used for extending the half-life of IL-31 in the serum are linked by a linker. In Some embodiments of the invention, the linker is a sequence of between 2-20 amino acids.

In some embodiments of the invention, the linker is a sequence of between 4-12 amino acids which form a cleavage site for enzymes such as MMP9/2, trypsin, PSA, cathepsins, kallikreins, serine proteases, caspases and others. Additional possible cleavage sites are presented in CHOI et al., "Protease-Activated Drug Development", Theranostics, Vol. 2(2), pp. 156-178 (found in http://www.thno.org/v02p0156.pdf). In some embodiments, the linker is between 6-8 amino acids and in some embodiments includes a cleavage site for enzymes such as MMP9/2, trypsin, PSA, cathepsins, kallikreins, serine proteases, caspases and/or others.

In some embodiments, the linker that comprise a cleavage site of MMP-9/2, cathepsin, trypsin, kallikreins, serine proteases, caspases or any other cleaving enzyme that can be added between IL-31 and IgG. For example, a sequence of the following amino acids between IL-31 and IgG may be provided: -Gly-Pro-Leu-Gly-Ile-Ala-Gly-Gln- (SEQ ID: No. 7, for MMP-9/2 cleaving site), -Lys-Lys-Phe-D-Ala-ε-maleimidocaproic acid (SEQ ID. No: 8, for cathepsin B cleaving site); -Lys-Gly-Ala-Ser-D-Arg-Phe-Thr-Gly- (SEQ ID: No. 9, for trypsin cleaving site); or ε-maleimidocaproic acid-Arg-Arg-Ser-Ser-Tyr-Tyr-Ser-Gly (SEQ ID No: 10, for PSA cleaving site).

Furthermore, the present invention encompasses nucleic acids encoding the fusion proteins described herein. In addition, vectors comprising these nucleic acids and cells transformed with theses vectors are encompassed by the present invention.

Briefly, the fused protein is prepared as follows: an expression construct (i.e., expression vector), which includes an isolated polynucleotide (i.e., isolated from a naturally occurring source thereof, e.g., SEQ ID NO: 2 or SEQ ID NO: 3 Gene ID 386653 (for human) and 76399 (for mouse) that comprises a nucleic acid sequence encoding the IL-31 amino acid sequence fused (optionally including a linker) in frame to a nucleic acid sequence encoding the IgG amino acid sequence e.g., AB776838 (for human, NCBI database) or DQ38154 (for mouse, NCBI database) or SEQ ID. No: 5 or SEQ ID. No. 4, respectively, positioned under the transcriptional control of a regulatory element, such as a promoter, is introduced into host cells.

For example, a nucleic acid sequence encoding an IL-31 amino acid sequence of the invention (e.g., SEQ ID NO:1 or SEQ ID NO:6, Gene ID. 386653 (for human) or 76399 (for mouse) is ligated in-frame to an immunoglobulin cDNA sequence (e.g., AB776838 (for human) and DQ38154 (for mouse).

In some embodiments of the invention, when a cleaving site for enzymes is required, a nucleic acid sequence encoding e.g. one or more of the amino acid sequences SEQ ID. Nos. 7-10, is added to the construct.

It will be appreciated that, ligation of genomic immunoglobulin fragments can also be used. In this case, fusion requires the presence of immunoglobulin regulatory sequences for expression. cDNAs encoding IgG heavy-chain constant regions can be isolated based on published sequences from cDNA libraries, derived from spleen or peripheral blood lymphocytes, by hybridization or by polymerase chain reaction (PCR) techniques. The nucleic acid sequences encoding the IL-31 amino acid sequence and immunoglobulin can be ligated in tandem into an expression construct (vector) that directs efficient expression in the selected host cells, further described hereinbelow. For expression in mammalian cells, pRK5-based vectors [Schall et al., Cell, 61:361-370 (1990)]; and CDM8-based vectors [Seed, Nature, 329:840 (1989)] can be used. The exact junction can be created by removing the extra sequences between the designed junction codons using oligonucleotide-directed deletional mutagenesis [Zoller et al, Nucleic Acids Res., 10:6487 (1982); Capon et al., Nature, 337:525-531 (1989)]. Synthetic oligonucleotides can be used, in which each half is complementary to the sequence on either side of the desired junction; ideally, these are 11 to 48-mers. Alternatively, PCR techniques can be used to join the two parts of the molecule in-frame with an appropriate vector.

Methods of introducing the expression construct into a host cell are well known in the art and include electroporation, lipofection and chemical transformation (e.g., calcium phosphate). See also Example 5 of the Examples section which follows, as well as in the Experimental procedures section therein.

The "transformed" cells are cultured under suitable conditions, which allow the expression of the chimeric molecule encoded by the nucleic acid sequence.

Following a predetermined time period, the expressed chimeric molecule is recovered from the cell or cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516-544].

Other than containing the necessary elements for the transcription and translation of the inserted coding sequence (encoding the chimera), the expression construct of the present invention can also include sequences engineered to optimize stability, production, purification, yield or effectiveness of the expressed fusion protein.

A variety of prokaryotic or eukaryotic cells can be used as host-expression systems to express the fusion protein coding sequence. These include, but are not limited to, microorganisms, such as bacteria transformed with a recombinant bacteriophage DNA, plasmid DNA or cosmid DNA expression vector containing the chimera coding sequence; yeast transformed with recombinant yeast expression vectors containing the chimera coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the chimera coding sequence Mammalian expression systems may also be used to express the chimera of the invention.

The choice of host cell line for the expression of the molecules depends mainly on the expression vector. Eukaroyotic expression systems are preferred (e.g., mammalian and insects) since they allow post translational modifications (e.g., glycosylation). Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient expression. CDM8-based vectors can be used to transfect COS cells by the DEAE-dextran method (Aruffo et al., Cell, 61:1303-1313 (1990); Zettmeissl et al., DNA Cell Biol. US, 9:347-353 (1990)]. If larger amounts of protein are desired, the molecules can be expressed after stable transfection of a host cell line (see Example 1 of the Examples section). It will be appreciated that the presence of a hydrophobic leader sequence at the N-terminus of the molecule will ensure processing and secretion of the molecule by the transfected cells.

It will be appreciated that the use of bacterial or yeast host systems may be preferable to reduce cost of production. However since bacterial host systems are devoid of protein glycosylation mechanisms, a post production glycosylation may be needed.

According to some embodiments, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant chimera molecule of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant protein is affected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Molecules of the present invention are preferably retrieved in "substantially pure" form. As used herein, "substantially pure" refers to a purity that allows for the effective use of the protein in the applications, described herein below.

Recombinant molecules of the present invention can be conveniently purified by affinity chromatography. The suitability of protein A as an affinity ligand depends on the species and isotype of the immunoglobulin Fc domain that is used in the chimera. Protein A can be used to purify chimeric molecules that are based on human .gamma.1, .gamma.2, or .gamma.4 heavy chains [Lindmark et al., J. Immunol. Meth., 62:1-13 (1983)]. Protein G is preferably used for all mouse isotypes and for human .gamma.3 [Guss et al., EMBO J., 5:1567-1575 (1986)]. The solid support to which the affinity ligand is attached is most often agarose, but other solid supports are also available. Mechanically stable solid supports such as controlled pore glass or poly (styrenedivinyl)benzene allow for faster flow rates and shorter processing times than can be achieved with agarose. The conditions for binding the chimeric molecules to the protein A or G affinity column are dictated entirely by the characteristics of the Fc domain; that is, its species and isotype. Generally, when the proper ligand is chosen, efficient binding occurs directly from unconditioned culture fluid. One distinguishing feature of chimeric molecules of this aspect of the present invention is that, for human .gamma.1 molecules, the binding capacity for protein A is somewhat diminished relative to an antibody of the same Fc type. Bound chimeric molecules of this aspect of the present invention can be efficiently eluted either at acidic pH (at or above 3.0), or in a neutral pH buffer containing a mildly chaotropic salt. This affinity chromatography step can result in a chimeric molecule preparation that is >95% pure. Medical grade purity is essential for therapeutic applications.

Other methods known in the art can be used in place of, or in addition to, affinity chromatography on protein A or G to purify chimeric molecules which include an immunoglobulin portion. Such chimeric molecules behave similarly to antibodies in thiophilic gel chromatography [Hutchens et al., Anal. Biochem., 159:217-226 (1986)] and immobilized metal chelate chromatography [Al-Mashikhi et al., J. Dairy Sci., 71:1756-1763 (1988)]. In contrast to antibodies, however, their behavior on ion exchange columns is dictated not only by their isoelectric points, but also by a charge dipole that may exist in the molecules due to their chimeric nature.

The above-described molecules are preferably non-immunogenic for maximizing therapeutic efficacy.

As used herein the term "non-immunogenic" refers to a substance that is substantially incapable of producing an immune response in a subject administered therewith. For example, non-immunogenic in a human means that upon contacting the chimeric molecule of this aspect of the present invention with the appropriate tissue of a human, no state of sensitivity or resistance to the chimeric molecule is demonstrable upon the second administration of the chimeric molecule after an appropriate latent period (e.g., 8 to 14 days).

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local, rather than systemic, manner, for example, via injection of the pharmaceutical composition directly into a specific tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with fillers such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

According to some embodiments of the invention, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (IL-31) effective to prevent, alleviate or ameliorate symptoms of a disorder (angiogenesis related disease or cancer) or prolong the survival of the subject being treated.

Determination of a therapeutically effective amount is well within the capability of those skilled in the art, and depends on the severity of the disease, its type, the mode of administration and the like.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

EXAMPLES

Experimental Procedures Used in the Examples
Cell Culture

MC38 murine colon carcinoma, and 4T1 murine breast carcinoma cell lines (ATCC, Manassas, Va., USA) and were used within 6 months of resuscitation. The cell lines were grown in Dulbecco's modified Eagle's medium (DMEM) supplemented with 10% fetal calf serum, 1% L-glutamine, 1% sodium pyruvate, and 1% streptomycin, penicillin and neomycin in solution (10 mg/ml, Biological Industries, Israel).

Cell Viability Alamar Blue™ Assay

Cell viability was evaluated quantitatively with the metabolic indicator dye AlamarBlue™ (Serotec Ltd., Oxford, UK), which determines the metabolic activity of cells and is used for cell viability and proliferation as previously described in Voloshin T, Gingis-Velitski S, Bril R, Benayoun L, Munster M, Milsom C, Man S, Kerbel R S, Shaked Y (2011) G-CSF supplementation with chemotherapy can promote revascularization and subsequent tumor regrowth: prevention by a CXCR4 antagonist (Blood 118 (12):3426-3435). Cells were harvested from sub-confluent cultures and re-plated (500-1,000 cells/well in a 96-well plate) in their designated medium and 10% AlamarBlue (AB) solution. In some experiments mouse or human recombinant IL-31 (Peprotek, Israel) was added in escalating concentrations (usually 0.5 ng-20 ng/ml). Results were corrected to background values of negative controls. Results are presented as a percent reduction of AB, calculated by the appropriate equation. All experiments were performed in triplicate, and data were presented as means±standard error.

Western Blot

Fifty μg of proteins were analyzed by 10% SDS/PAGE gel, transferred to a nitrocellulose membrane, and subsequently blotted with mouse IL-31 antibody (5 μg/ml, Abcam) or human IL-31 antibody (5 μg/ml, Abcam), and normalized with actin mouse monoclonal antibody (1:5,000, MP Biomedicals).

Downregulation of IL-31 by shRNA

Four sequence shRNA clones specific to murine IL-31 or shRNA control (empty scrambled vector) were constructed by Applied Biological Materials (Canada). The cells were transfected at a confluency of 60%. Transfection was achieved using FuGENEV R 6 (Roche, Penzberg, Germany) according to the manufacturer's instructions. 48 hours post-transfection, cells were incubated in growth medium containing puromycin (1 μl/ml) to select for stable transfectants. After two weeks of selection, the IL-31 shRNA-mediated gene silencing was assessed for each clone using western blot analysis.

Flow Cytometry

Tumor cells, macrophages, or cells obtained from tumors followed by single cell suspension procedure as previously described in Adini A, Fainaru O, Udagawa T, Connor K M, Folkman J, D'Amato R J (2009) Matrigel cytometry: a novel method for quantifying angiogenesis in vivo. J Immunol. Methods 342 (1-2):78-81, were immuno stained with the following antibody mixtures: For the analysis of endothelial cells: CD45−/CD31+/VEGFR2+; for MDSCs: Gr-1+, CD11b+; for M1 macrophages (F4/80+CD11c+CD206−) and for M2 macrophages (F4/80+CD11c−CD206+). All antibodies were purchased from BD Biosciences or BioLegend (San Diego, Calif.). The experiments were performed on Cyan-ADP flow cytometer (Beckman Coulter, Switzerland) and analyzed with Summit Version 4.3 (Beckman Coulter).

Tissue Processing and Immunostaining

Tumors (were embedded in OCT and were subsequently sectioned. 10 μm cryosections were used for the analysis of microvessel density (MVD) and macrophage colonization in the tissue. For endothelial cells, anti-CD31 antibody was used as a specific endothelial marker (1:200, BD Biosciences) along with a Cy3-conjugated secondary antibody (1:500, Jackson immunoresearch laboratories). For macrophages, anti-F4/80 conjugated to FITC antibody was used as a specific macrophage marker (1:200, BD Biosciences). The number of vessel structures or cells per field were counted and plotted. (At least 5 fields per tumor, n>20 fields per group).

Tumor Models

MC38 murine-colorectal carcinoma cells ($2\times10^6$) were subcutaneously injected into the flank of 5- to 6-week-old female BALB/c mice (Harlan, Israel). 4T1 murine-breast carcinoma cells ($5\times10^5$) were orthotopically injected into the mammary fat pad of 6-week-old female BALB/c mice. Tumor size was assessed regularly with Vernier calipers using the formula width$^2\times$length$\times0.5$. All animal studies were performed in accordance with the Animal Care and Use Committee of the Technion-Israel Institute of Technology.

Osmotic Pumps

Osmotic minipumps were used in vivo to allow the continuous administration of recombinant IL-31 to mice for a period of two weeks, as per the manufacturer's instructions. Briefly, when tumors reached 150-200 mm$^3$, treatment was initiated by subcutaneous implantation of osmotic minipump (#1002, Alzet, Cupertino, Calif.) loaded with recombinant mouse IL-31 (in a total concentration of 0.7 μg per day) or PBS as a vehicle control. The procedure was performed under sterile conditions. The mice were sacrificed 14 days after pump implantation and further assessed as described in the text.

IL-31-IgG Construct

The corresponding DNA sequence of mature IL-31 protein with its signal peptide for secretion was synthesized based on gBlocks Gene Fragment technology from IDT, and inserted into NSPI expression vector. Mouse IgG1 heavy chain (hinge-CH2-CH3) was cloned downstream to IL-31 and upstream to myc-His6. Briefly, total RNA was isolated from mouse spleen using RNeasy Mini Kit (Qiagen). Single-stranded cDNA was synthesized using M-MLV reverse transcriptase (Promega) according to manufacturer's instructions. Mouse IgG1 heavy chain (hinge-CH2-CH3) was amplified using PCR. The primers used were: sense (5-TACCGCTCGAGGTGCCCAGGGATTGTGGTTG-3) (SEQ ID NO: 11) and antisense (5'-CGTTCGAATTTAC-CAGGAGAGTGGG-3) (SEQ ID NO: 12). The PCR fragment provides a size of ~700 Kb. The resulting plasmid, NSPI-IL-31-mIgG-myc-His, was checked by restriction mapping and sequencing. Plasmids were transfected into Chinese hamster ovary (CHO) cells using FuGENEV R 6 (Roche, Penzberg, Germany) in accordance with the manufacturer's instructions. After 48 hours, cells were incubated in growth medium containing puromycin (1 μl/ml) to select for stable transfectants. Conditioned medium from CHO transfected cells were tested for inhibition of cell viability.

Statistical Analysis

Data are presented as mean standard deviation (SD). Statistically significant differences were determined by two-tailed Student's t test or one-way ANOVA as described in the text. Significance was set at values of *, $0.05>p>0.01$; , $0.01>p>0.001$; and *$p<0.001$.

Example 1

IL-31 Affects Tumor Cell Proliferation and Viability

Cell lysates from tumor cell lines including EMT6, P3, MPC, CT26, B16, LLC, K7M2, 4T1 and MC38 were analyzed for IL-31 as well as IL-31 receptor (IL-31R) expression using western blot.

As detailed herein and as presented in FIG. 1(A-G), IL-31 inhibits tumor cell proliferation in IL-31 dependent manner. FIG. 1A shows cell lysates from tumor cell lines that were analyzed for IL-31 as well as IL-31 receptor (IL-31R) expression using western blot analysis. Particularly, the results in FIG. 1A show that while IL-31 was highly expressed in MC38 and K7M2 cell lines, it was minimally expressed in P3, MPC, B16 and 4T1 cells. In addition, IL31R shows high expression patterns in most non-metastatic cells when compared to highly metastatic cells, which show a low expression pattern.

Figures 1B, 1C:
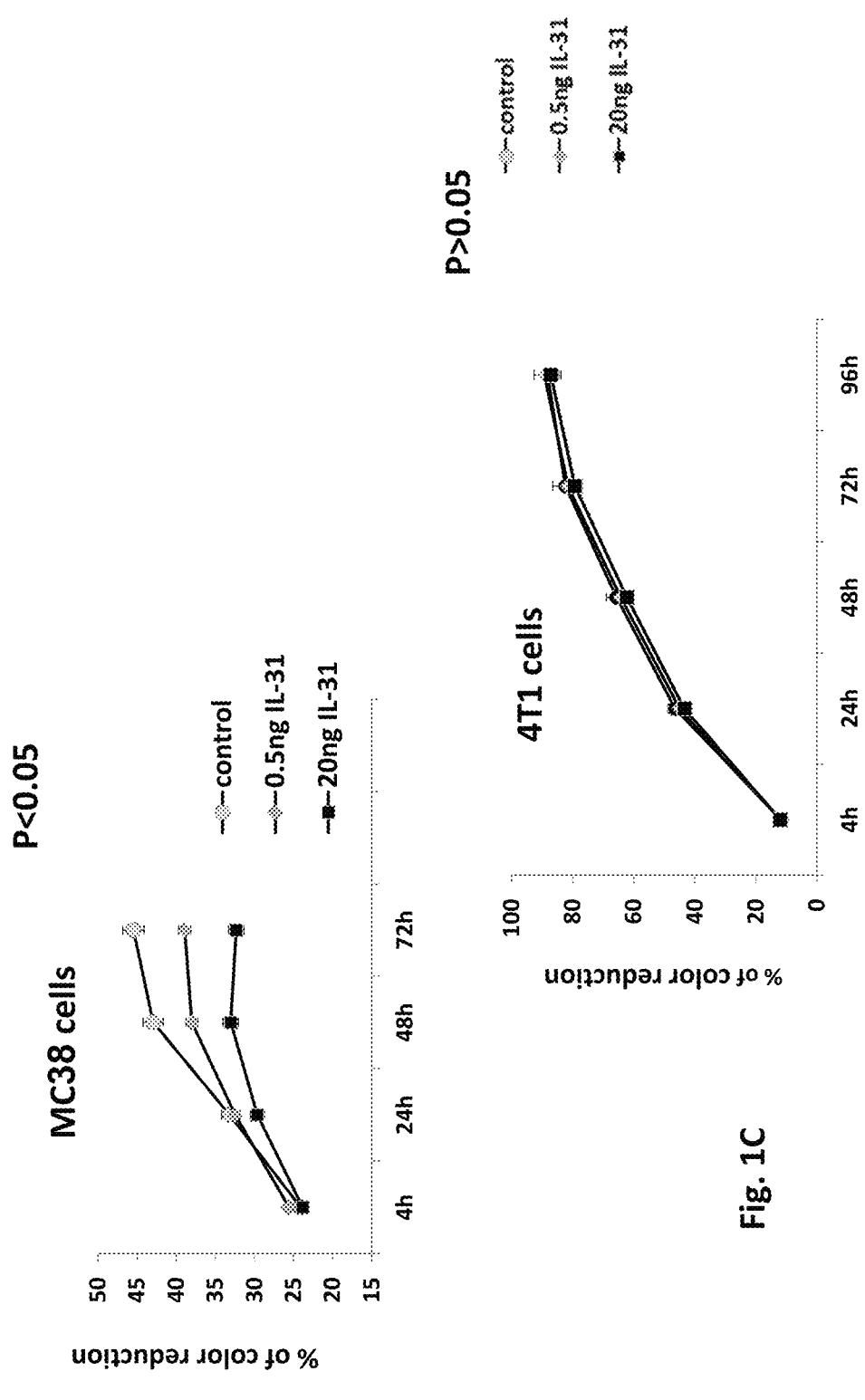
Figure 1E:
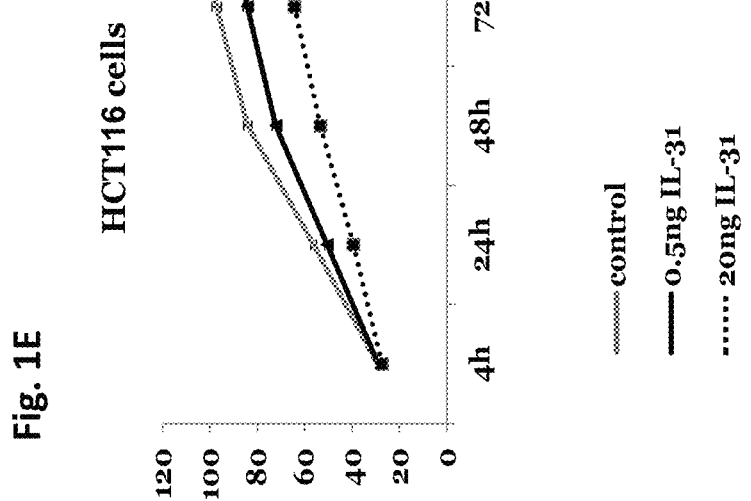
Figure 1D:
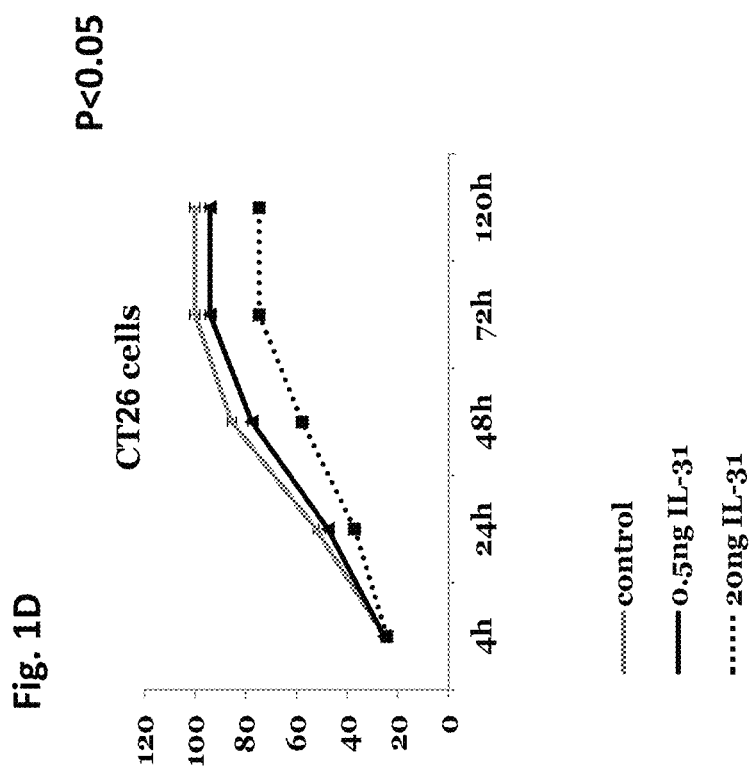
Figure 1F:
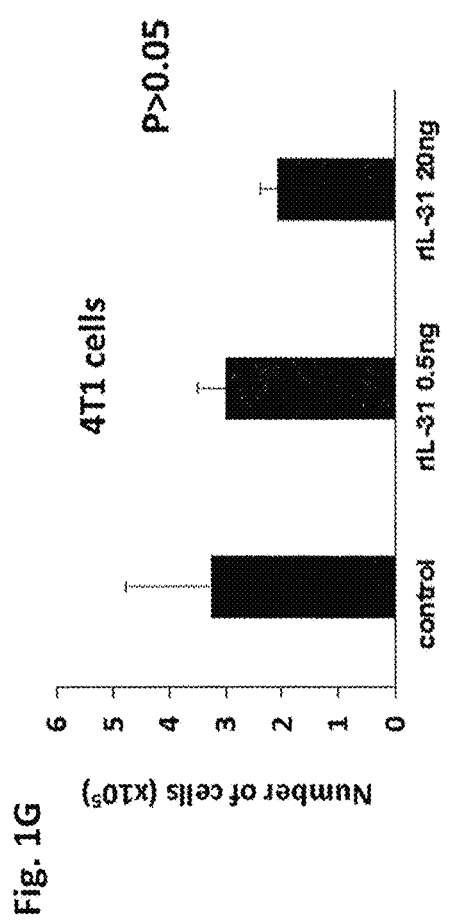
Figure 1G:
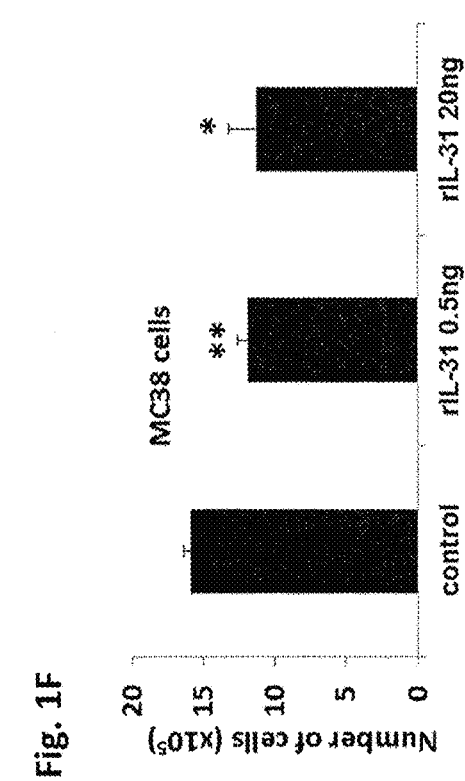

Next, MC38 and 4T1 cell lines were used as two representative cells which either express IL-31 or not, respectively, in order to further evaluate the possible effect of IL-31 on tumor cell proliferation and viability. Cell viability was assessed in the presence of recombinant IL-31 (rIL-31) by Alamar Blue. The results in FIGS. 1B-E demonstrates that the addition of rIL-31 strongly and significantly inhibited cell proliferation in MC38, CT26 and HCT116 when compared to control, an effect which was absent in the case of 4T1 cells (FIG. 1C). In addition, cell count was performed on these cells, and revealed that the number of viable cells was significantly reduced in MC38 in the presence of IL-31, but not in 4T1 tumor cells cultured with IL-31 (FIGS. 1F and 1G). These results suggest that IL-31 affects cell viability by inhibiting cell proliferation but only in some tumor cell lines, suggesting a distinct dependency of tumor cells on IL-31 and/or IL-31R expression.

Example 2

Lack of IL-31 in Tumor Cells Promotes Tumor Growth and Angiogenesis

To further confirm the activity of IL-31 on tumor cells in vivo, IL-31 was silenced in MC38 cells using RNAi technique.

Figure 2B:
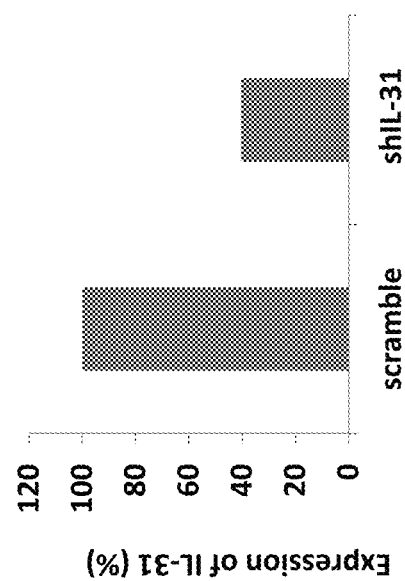
FIG. 2B is a graph showing the percentage of reduction of IL-31 expression in MC38 cells transfected with shIL-31 plasmid or with scrambled plasmid, as assessed by densitometry.
Figure 2A:
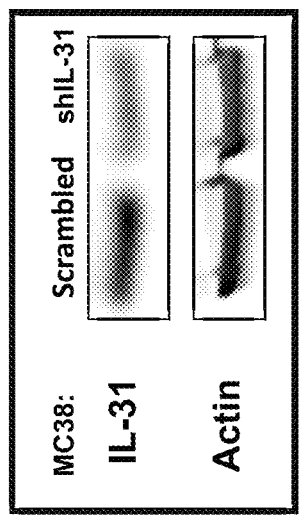
FIG. 2A is a Western blot image comparing IL-31 expression in lysates of MC38 transfected with shIL-31 plasmid or with scrambled plasmid.

As related to in detail herein, FIG. 2 presents shRNA for IL-31 inhibits the expression of IL-31 in tumor cells. FIG. 2A shows lysates of MC38 murine colon carcinoma cells after they were stably transfected with scramble plasmid or plasmid containing shRNA for IL-31 were evaluated for IL-31 expression using western blot analysis. The graph in FIG. 2B shows the percentage of reduction in IL31 expression in MC38 shIL-31 after it was normalized to its expression in scrambled control MC-38, as assessed by densitometry.

As can be seen in FIG. 2B, the expression level of IL-31 in MC38 shIL-31 cells was reduced by more than 60% compared to scrambled MC38 control cells.

Figure 3A:
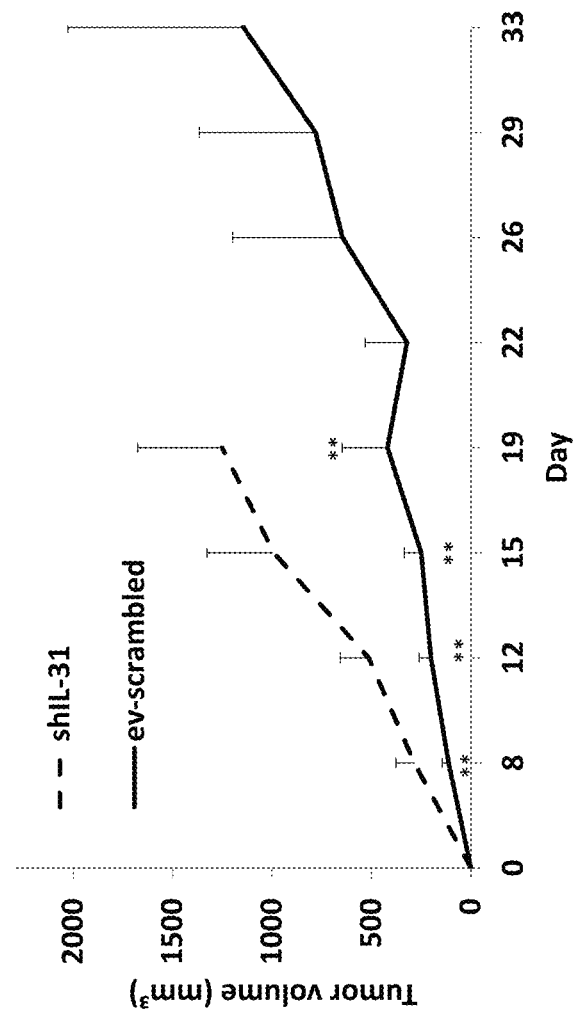
FIG. 3A compares tumor size ($mm^3$) in mice that were injected subcutaneously into the flanks with MC38 cells transfected with either shIL31 or scrambled plasmid.
Figure 3C:
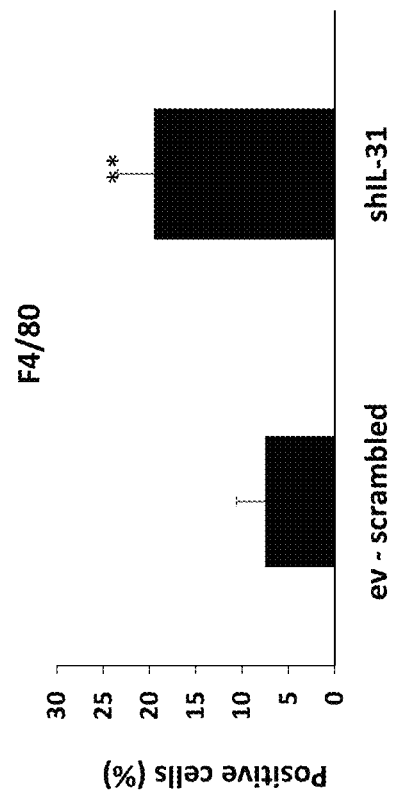
FIGS. 3C and 3D present the number of macrophages (F4/80+ cells) (FIG. 3C) and endothelial cells (FIG. 3D) in tumor from mice injected with MC38 cells transfected with shIL-31 or scrambled plasmids.
Figure 3D:
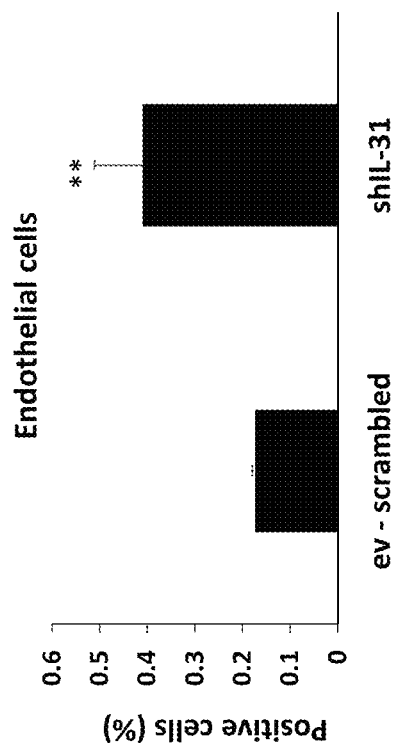

As further detailed herein, FIG. 3 presents the lack of IL-31 expression promotes tumor growth, angiogenesis and TAMs. Two million scramble control MC38, or its shIL-31 MC38 counterparts cells were injected subcutaneously into the flanks of C57Bl/6 mice. In FIG. 3A tumor growth was assessed regularly using a caliper. At end point, tumors were removed, sectioned and then immunostained with CD31, as an endothelial cell marker (FIG. 3B). Nuclear staining is designated by DAPI. In a parallel experiment, tumors were removed at end point and prepared as single cell suspension for the evaluation of endothelial cells (CD31+ cells) and macrophages (F4/80+ cells) using flow cytometry. The percentage of (FIG. 3C) CD31+ cells and (FIG. 3D) F4/80+ cells are presented. **, $0.05<p<0.01$ (FIGS. 3 C-D).

The results in FIG. 3A show that tumor growth was significantly enhanced in MC38 shIL-31 tumors when compared to their scrambled MC-38 counterparts. At the end point, tumors were removed and analyzed for microvessel density (MVD). A significant increase in MVD was observed in tumors from MC38 siIL-31 cells when compared to control tumors (FIG. 3B). In addition, large vessel structures were detected in tumors from MC38 shIL-31 tumors when compared to MC38 control counterparts (FIG. 3B). These results were further confirmed when the tumors were prepared as single cell suspension and analyzed by flow cytometry to CD31.

Recent studies indicated that bone marrow derived cells (BMDC) colonizing tumors may affect angiogenesis. Tumor associated macrophages (TAMs), for example, have been found to contribute significantly to tumor angiogenesis and subsequently promote tumor growth. Accordingly, macrophage colonization of tumors from MC38 shIL-31 cells was compared to control tumors. The number of macrophages (F4/80+ cells) and endothelial cells (CD31+ cells) was significantly higher in shIL-31 tumors when compared to ev-scrambled control tumors (FIGS. 3C and 3D). Taken together, these results suggest that the lack of IL-31 in tumors that previously expressed IL-31 promoted tumor growth, increased angiogenesis, and supported macrophage colonization of tumors.

Example 3

IL-31 Induces Anti-Tumor Activity in Both MC38 and 4T1 Tumors

Figure 4B:
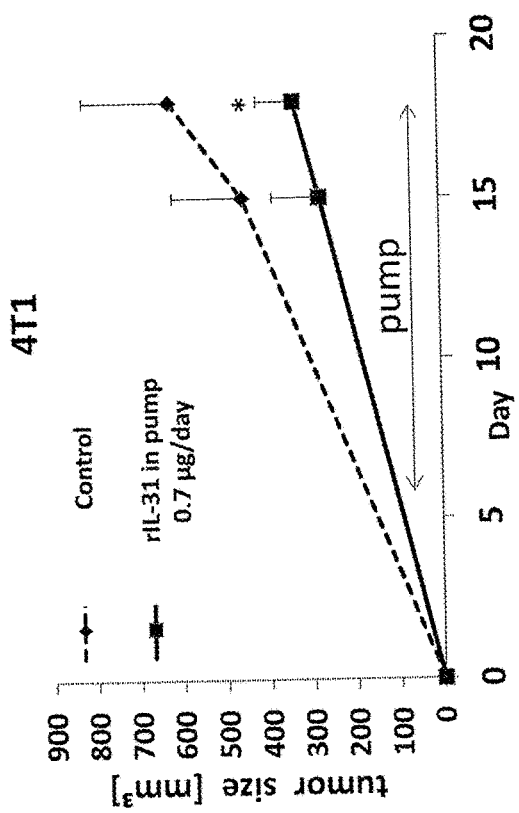
FIG. 4B shows the tumor size ($mm^3$) in mice implanted with 4T1 cells to the mammary fad pad and infused with minipump containing either rIL-31 or PBS (control)
Figure 4A:
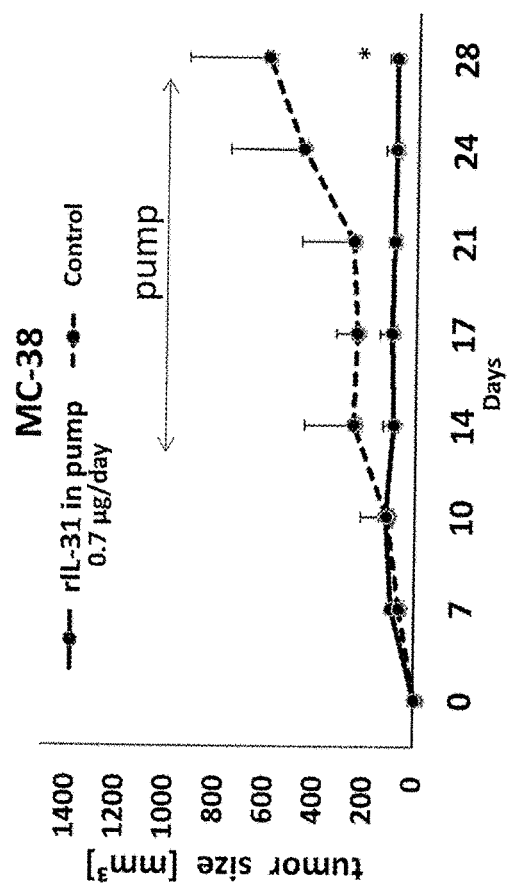
FIG. 4A shows the tumor size ($mm^3$) in mice implanted with MC38 cells into the flank and implanted with minipump containing either rIL-31 or PBS (control)
Figures 4C, 4D:
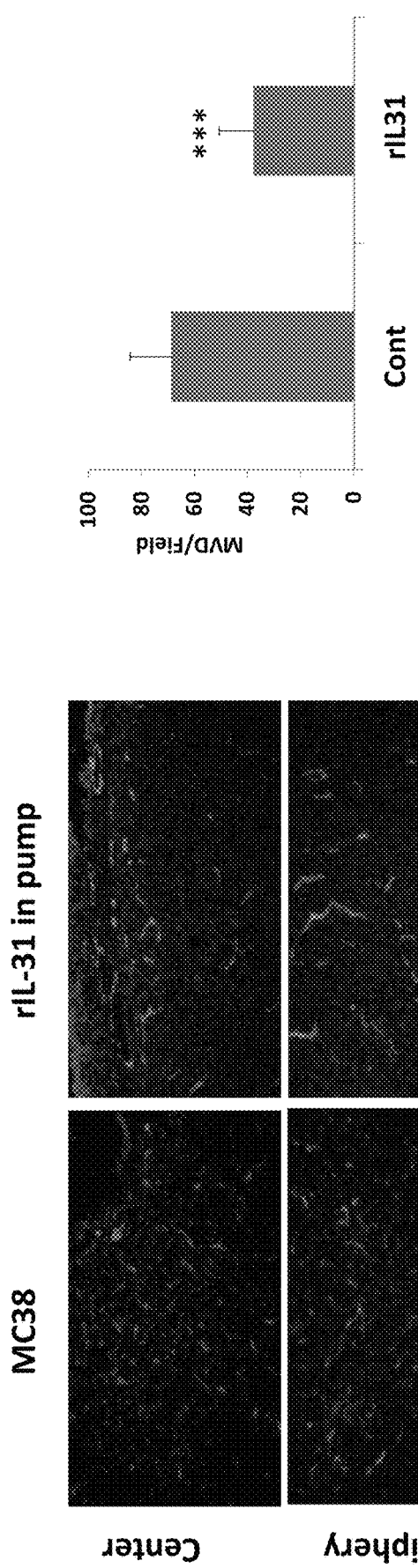
FIG. 4C compares microvessel density (MVD) in tumors that were removed from the mice implanted with MC38 and infused with either rIL-31 or PBS (control). The tumors were removed, sectioned and immune-stained with CD 31; nuclear staining was designated by 4',6-diamidino-2-phenylindole (DAPI)
FIG. 4D is a graph comparing MVD levels in tumors from mice implanted with MC38 and infused with either 0.7 µg/day rIL-31 or PBS (control).

As detailed herein, FIGS. 4A-I present inhibition of tumor growth, angiogenesis, and metastasis by IL-31. Two million of MC38 cells were implanted into the flanks of C57Bl/6 mice and half a million 4T1 cells were implanted into the mammary fad pad of BALB/c mice and were left to grow until they reached 150-200 mm$^3$, at which point the mice were implanted with minipumps containing PBS (control) or 0.7 µg/day recombinant IL-31 (rIL-31). Tumor growth was assessed regularly for (FIG. 4A) MC-38 and (FIG. 4B) 4T1. To test whether adding recombinant IL-31 can inhibit the growth of tumors, both MC38 cells, which are known to express IL-31, as well as 4T1cells, which do not express IL-31, were used. To this end, two million MC38 cells were subcutaneously implanted into the flanks of C57/Black mice (n=5/group) and half a million 4T1 cells were orthotopically implanted into the mammary fad pad of BALB/c mice (n=5/group). When tumors reached a size of ~150 mm$^3$, recombinant mouse IL-31 was continuously infused into the mice using osmotic pumps as explained above (n=5/group). The subcutaneously implanted osmotic minipumps were loaded with recombinant IL-31 that was released at a dose of 0.7 µg per day. Minipumps loaded with vehicle control (PBS) were used in control mice (n=5). Tumor growth was assessed regularly or at end point. In both mice groups, the continuous infusion of IL-31 resulted in a significant reduction in tumor size when compared to control tumors (FIGS. 4A and 4B). In addition, at end point, MC38 tumors were removed, sectioned and then (FIG. 4C) immunostained with CD31, as an endothelial cell marker. Nuclear staining is designated by DAPI. FIG. 4D shows quantification of the number of microvessels is presented in the graph.

Figure 4E:
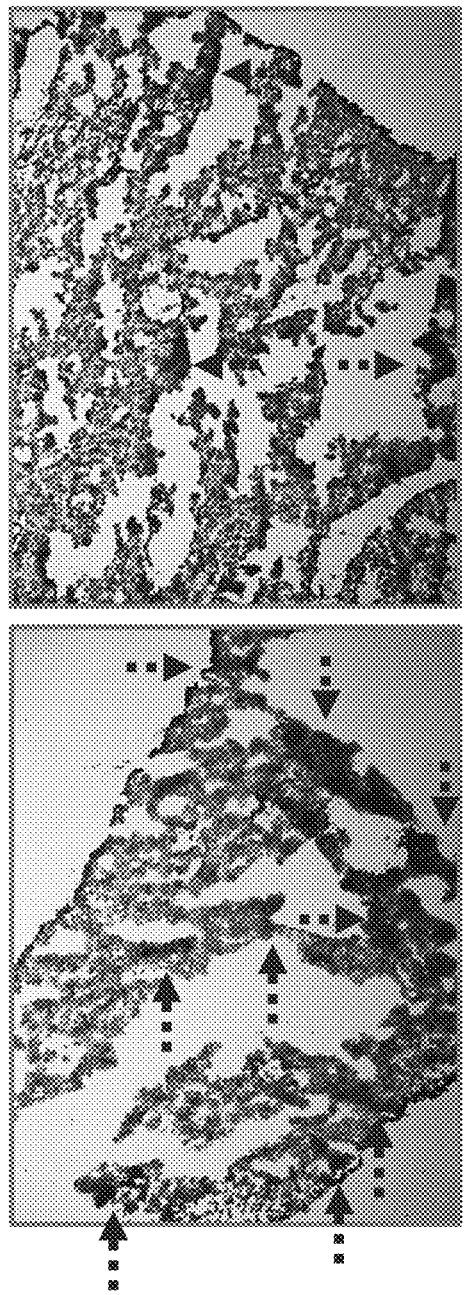

When MC38 tumors were removed and assessed for microvessel density (MVD), a decreased MVD was observed in tumors from mice that underwent IL-31 infusion when compared to control those injected with vehicle control (see in FIGS. 4C and 4D). Importantly, since the 4T1 tumor model is known to aggressively metastasize to the lungs of mice, at end point, tumors from all groups (n=5 mice/group) were removed and lungs were analyzed for metastatic lesions. In the case of 4T1 tumors, at end point, lungs were removed from the mice and assessed for metastatic lesions using H&E staining of lung sections (FIG. 4E). As depicted in FIG. 4E, a significant lower number of lung metastatic lesions were observed in mice infused with recombinant IL-31 when compared to lungs from mice infused with PBS. Collectively, these results suggest that the continuous infusion of mouse IL-31 has a numerous anti-tumor activities on tumor and its metastatic sites.

Figure 4G:
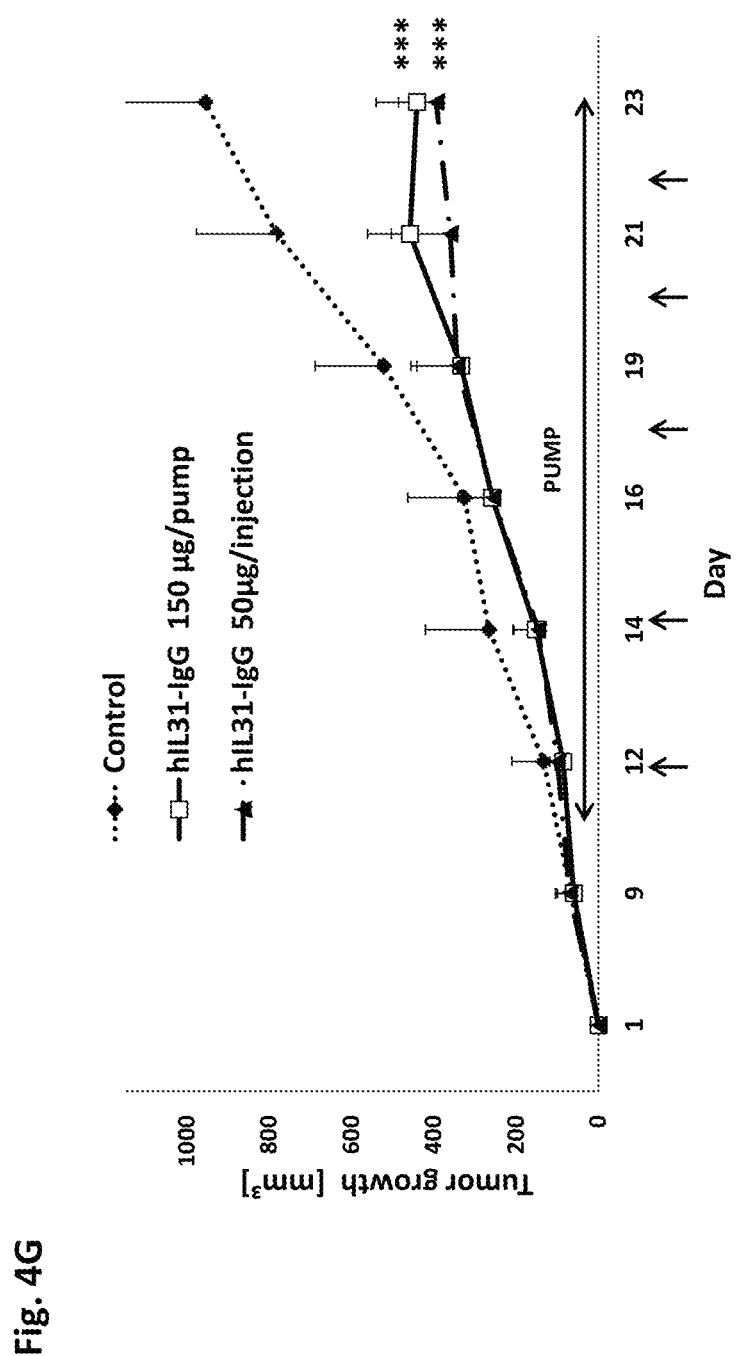
FIG. 4G shows tumor growth ($mm^3$) in NOD-SCID mice that were implanted with HCT116 cells ($2 \times 10^6$ cells; n=5 mice/group). When the tumors reached a size of 50 $mm^3$, the mice were either implanted with pumps containing 150 µg hIL31-IgG protein or injected ip twice a week with 50 µg hIL-31-IgG. Tumor growth was assessed over time.
Figure 41:
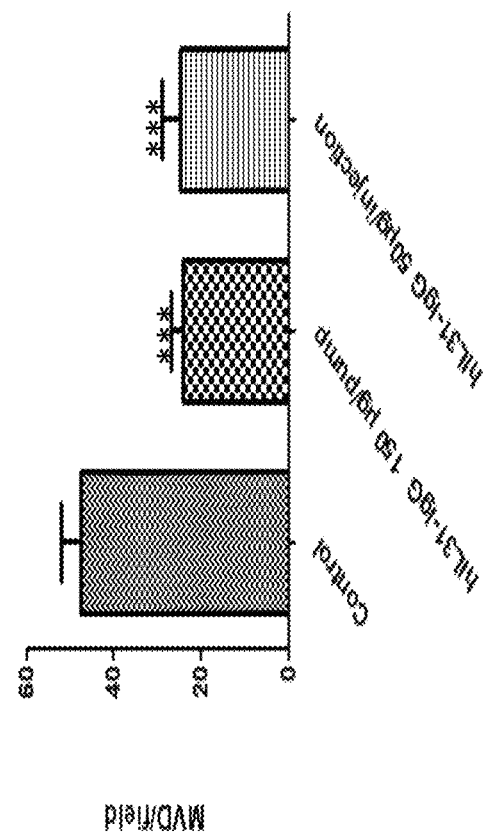

In FIG. 4F quantification of the number of metastatic lesions per field is provided. ***, p<0.001. In FIG. 4G NOD-SCID mice were implanted with HCT116 human colon carcinoma cells ($2 \times 10^6$ cells; n=5 mice/group). When the tumors reached a size of 50 mm$^3$, the mice were either implanted with pumps containing 150 μg hIL31-IgG protein or injected ip twice a week with 50 μg hIL-31-IgG. Tumor growth was assessed over time. The results show that both treatment methodologies resulted in a significant inhibition in tumor growth. After 2 weeks of treatment tumors were removed and sectioned. Tumor sections were stained for CD31, an endothelial cell marker, and the microvessel density was evaluated, by counting the number of vessels per field. As shown in the figure, the number of microvessels in the treated tumors was significantly lower than their numbers in control tumors. (FIGS. 4H-I) HCT116 tumors were removed at the end point, after mice were treated with hIL-31-IgG for 2 weeks either by pump or by IP injections. Tumors were sectioned and stained for CD31 (an endothelial cell marker—in red) FIG. 4H. Quantification of the number of vessels—microvessel density (MVD) per field is provided in FIG. 4I. As seen in FIGS. 4H-I, tumors from mice treated with IL31-IgG (either by injection or in pump) have lower microvessel density than control tumors, suggesting an anti-angiogenic activity of IL-31.

Example 4

Macrophages are Skews Towards M1 Phenotype in the Presence of IL-31

The in vivo results further suggested that IL-31, in addition to its effects on the tumor vasculature and the inhibition of tumor cell viability, as shown in vitro, may act also as a factor that can alter the macrophage colonization of tumors. In order to assess whether IL-31 may alter the phenotype properties of macrophages, an experiment focused on two specific macrophage phenotypes, known as pro-inflammatory M1 (CD206−/CD11c+) phenotype and anti-inflammatory M2 (CD206+/CD11c−) phenotype, was conducted. To this end, J774 murine macrophage cell lines were cultured in the presence or absence of recombinant IL-31 for 48 hours. Subsequently, they were analyzed by flow cytometry for the expression of M1 and M2 macrophages.

Figure 5C:
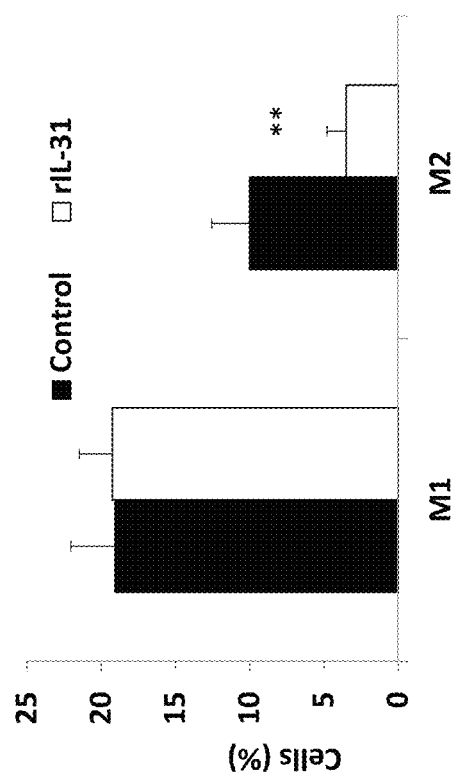
FIG. 5C is a graph comparing the number of M1 macrophage phenotype and M2 macrophage phenotype in a single cell suspension from MC38 tumors that were implanted in the flanks of C57Bl/6 mice. When tumors reached 150-200 $mm^3$, mice were implanted with mini-pumps containing PBS (control) or recombinant IL-31 in a dose of 0.7 µg/day (rIL-31). The percentage of M1 and M2 macrophages colonizing tumors were analyzed using flow cytometry.
Figure 5A:
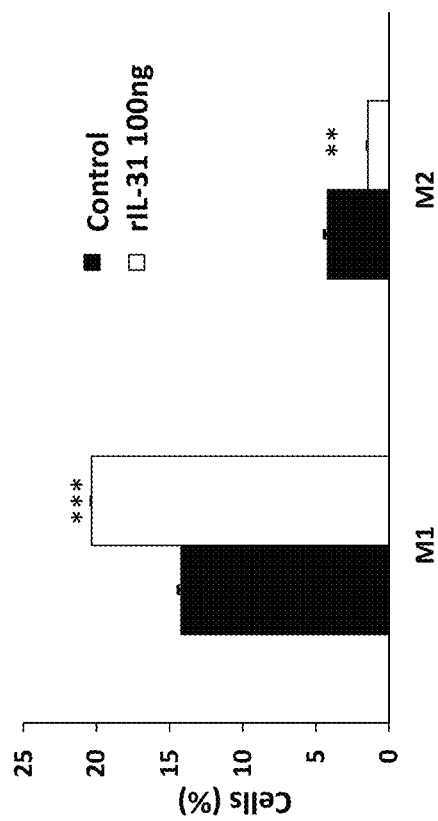
FIG. 5A is a graph comparing the number of M1 macrophage phenotype and M2 macrophage phenotype in J774 cells cultured in the presence and absence of rIL-31 (100 ng); cells were immune-stained with F4/80, CD206, and CD11c to evaluate the percentage of M1 (CD11c+/CD206−) and M2 (CD11c−/CD206+) macrophages.
Figure 5B:
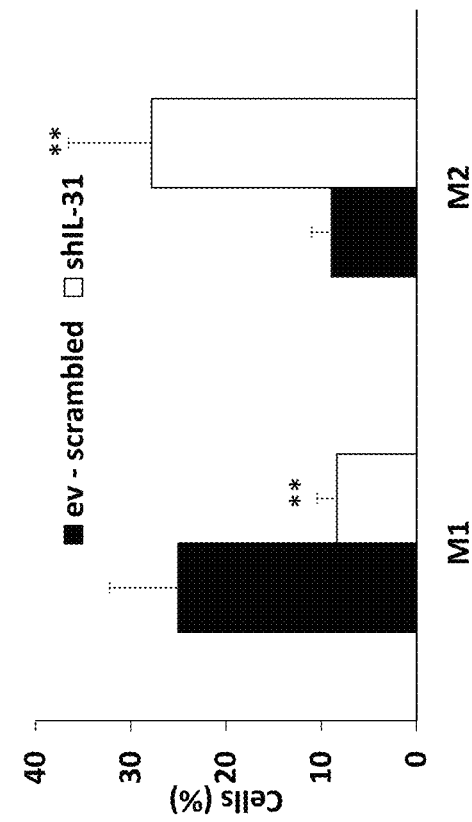
FIG. 5B is a graph comparing the number of M1 macrophage phenotype and M2 macrophage phenotype in a single cell suspension from MC38 tumors implanted in C57Bl6 which, either express IL-31 (ev-scrambled) or not (shIL-31), and that were let to grow until the endpoint. The percentage of M1 and M2 macrophages colonizing tumors were analyzed using flow cytometry.

As detailed herein, FIGS. 5A, 5B and 5C present: IL-31 promotes macrophage polarization into M1 phenotype. (FIG. 5A) J774 murine macrophages cell lines were cultured in serum-free medium in the presence or absence of 100 ng recombinant IL-31 for 24 hours. After 48 hours, cells were immunostained with F4/80, CD206, and CD11c to evaluate the percentage of M1 (CD11c+/CD206−) and M2 (CD11c−/CD206+) macrophages. Graphs are provided. (FIG. 5B) MC38 tumors implanted in C57Bl6 which, either express IL-31 (ev-scrambled) or not (shIL-31), were let to grow until endpoint. Tumors were then removed and prepared as single cell suspension, and the percentage of M1 and M2 macrophages colonizing tumors were analyzed using flow cytometry. (FIG. 5C) Two million MC38 cells were implanted in the flanks of C57Bl/6 mice. When tumors reached 150-200 mm$^3$ mice were implanted with mini-pumps containing PBS (control) or recombinant IL-31 in a dose of 0.7 μg/day (rIL-31). At end point, tumors were removed and prepared as single cell suspension. The percentage of M1 and M2 macrophages colonizing tumors were analyzed using flow cytometry. , 0.05<p<0.01; *, p<0.001.

The results in FIG. 5A revealed a significant increase in M1 phenotype and a decrease in M2 phenotype in J774 cells cultured in the presence of IL-31 when compared to control cells.

Next, the colonization of macrophages in tumors was re-examined in mice bearing MC-38 tumors (n=5/group), which either do not express IL-31 (shIL31 tumors) or that were implanted in mice infused with recombinant IL-31 (n=5/group), both compared to control mice (n=5). The results in FIG. 5B show a reversed phenotype of M1 and M2 macrophages colonizing shIL-31 and control tumors, namely, the percentage of M1 macrophages was significantly reduced and the percentage of M2 macrophages was significantly increased in the microenvironment of tumors lacking IL-31 expression (shIL-31) when compared to control tumors. In addition, tumors from mice infused with recombinant IL-31 revealed that the percentage of M2 macrophages but not M1 macrophages colonizing MC38 tumors was significantly reduced in mice infused with recombinant IL-31 when compared to mice infused with vehicle control (FIG. 5C). Taken together, the results further suggest that both in vivo and in vitro, IL-31 reduces the anti-inflammatory macrophage phenotype in tumors.

Example 5

IL-31-IgG Construct Inhibits the Proliferation of Tumor Cells

Since the continuous infusion of IL-31 revealed anti-tumor activities a construct in which IL-31 was conjugated to immunoglobulin in order to increase the half-life of conjugated cytokine was assessed. IL-31-IgG was prepared by cloning a plasmid containing IL-31 conjugated with Mouse IgG1 heavy chain (hinge-CH2-CH3) to give a product of IL-31-mIgG-myc-His. The plasmid was transfected into Chinese hamster ovary (CHO) cells. Conditioned medium from transfected CHO cells was then placed on MC38 cells and then tested for activity using Alamar Blue assay as detailed in Example 1.

Figure 6:
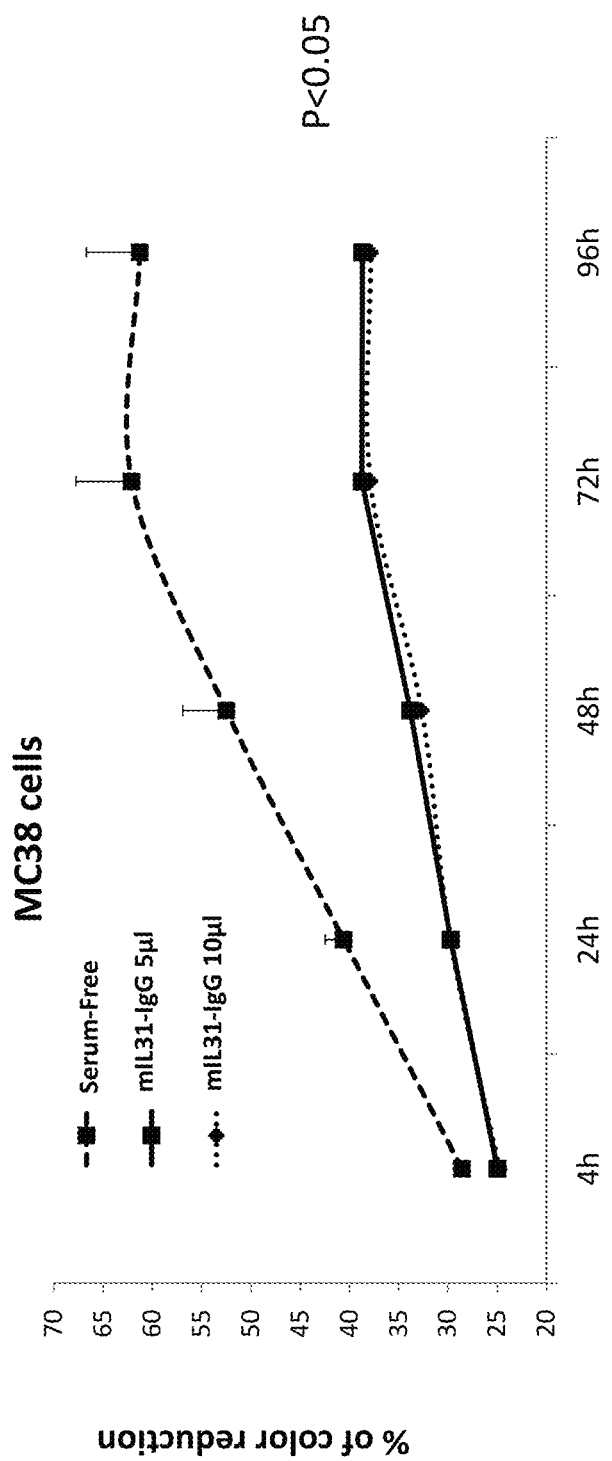
FIG. 6 presents an assessment of MC38 cell viability using Alamar Blue assay. The cells were cultured in the presence of escalating doses of mIL-31-IgG. A reduction in cell viability was observed with the increased concentration of IL-31-IgG.

As detailed herein, FIG. 6 presents MC38 cell viability that was assessed using Alamar Blue assay. The cells were cultured in the presence of escalating doses of mIL-31-IgG. A reduction in cell viability was observed with the increased concentration of IL-31-IgG.

Example 6

Tumors can be Affected by the Treatment with the IL-31 Ligand, which Inhibits Tumor Cell Viability.

The expression levels of IL-31R (receptor) on various human colon and breast carcinomas from cancer patients revealed that many but not all tumors express IL-31R. Thus, such tumors can be affected by the treatment with the ligand IL-31 which inhibits tumor cell viability as shown in vitro.

Figure 7:
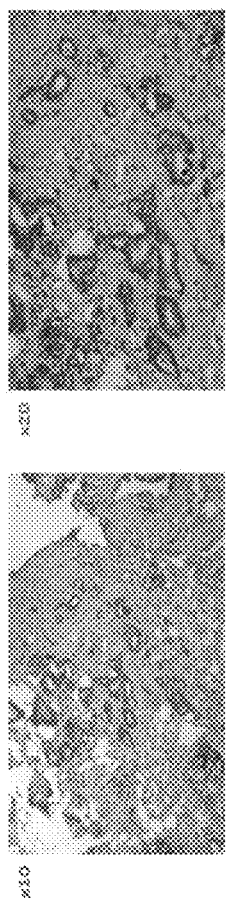
FIG. 7 shows an example of staining image for breast cancer biopsy P-12855/11. High intensity of IL-31R expression is observed in carcinoma cells of the breast cancer biopsy.

Table 1 is a summary of biopsies from colon and breast cancer patients that were immunostained for IL-31R. The table show that most biopsies have positive (P) staining for IL-31R (N-is referred to negative staining). Intensity of staining is presented by the number of "+" signs in each sample. FIG. 7 provides an example of staining of one of the biopsies, indicating the high expression of IL-31R (in black) in carcinogenous tissue. Table 2 provides a tissue array of human normal and tumor tissue of various origins, indicating the expression levels of IL-31R in each tissue. High expression of IL31R is presented in carcinogenous tissues of all origins. However, in some normal tissue high expression of IL31R is also presented. "T" stands for tumor tissue. "N" stands for normal tissue.

TABLE 1 biopsies from colon and breast cancer patients that were immunostained for IL-31R

| Tissue type/Patient number | Staining (P/N) | Staining Intensity |
|---|---|---|
| Colon Cancer Biopsies | 12/15 Positives | |
| 14-09085 | P | ++ |
| 14-07461 | P | ++++ |
| 14-05245 | P | ++ |
| 14-05087 | P | ++ |
| 14-04018 | P | ++++ |
| 14-03717 | N | - |
| 14-02841 | P | + |
| 14-01064 | N | - |
| 14-00670 | P | ++ |
| 14-00154 | P | ++ |
| 14-09531 | P | ++++ |
| 14-09428 | N | + |
| 14-09434 | P | +++ |
| 14-09431 | P | ++++ |
| 14-09087 | P | +++ |
| Breast Cancer | 6/10 positives | |
| 68482/10 | N | - |
| 19197/11 | P | + |
| 14994/14 | N | - |
| 32530/10 | N | - |
| 5378/10 | P | ++ |
| 8603/13 | N | - |
| 22782/14 | P | ++ |
| 49549/12 | P | +++ |
| 29788/11 | P | +++ |
| 9757/13 | P | + |
| Breast Cancer Biopsies | 4/5 positives | |
| 34735/12 | P | ++++ |
| 48685/09 | P | +++ |
| 28176/10 | P | ++ |
| 1637/10 | N | - |
| 12855/11 | P | +++ |

TABLE 2

IL-31R in human normal and tumor tissue of various origins

| Cancer Survey Tissue Array Tissue type | Tumor (T) | Normal (N) | Remark |
|---|---|---|---|
| Breast | 4/6 | 1/2 | Most T are mild |
| Colon | 6/7 | 2/3 | Most T are mild |
| Lung | 8/8 | 3/3 | Different intensities in T mild stain in N |
| Kidney | 8/8 | 5/5 | N is also strong |
| Ovary | 8/9 | 1/4 | Different intensity in T |
| Endometrium | 5/5 | 2/3 | T are intense |
| Stomach | 5/8* | 0/0 | *2 T-cores are connective tissue |
| Skin | 6/6 | 1/2 | |
| Liver | 5/6* | 5/5 | *1 T core is connective tissue |

The expression levels of IL-31R on various human colon and breast carcinomas from cancer patients revealed that many but not all tumors express IL-31R. Thus, such tumors can be affected by the treatment with the ligand IL-31 which inhibits tumor cell viability as shown in vitro.

Example 7

IL-31-IgG is Stabilized for at Least 72 h in Peripheral Blood.

Figure 8F:
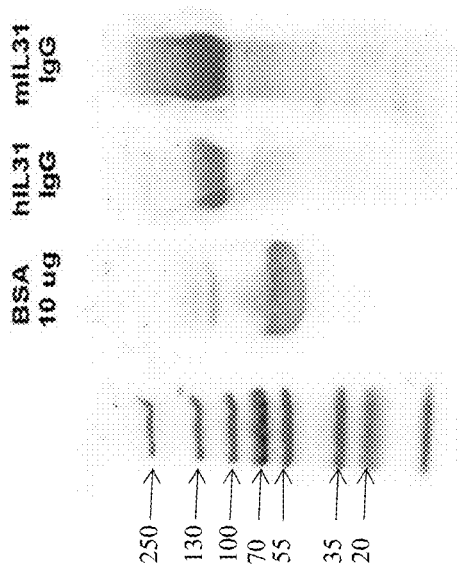
FIGS. 8 (A-H): shows that IL-31-IgG is stabilized for at least 72 hours in peripheral blood. 293T cells were transfected with the IL-31-Ig construct.
(FIG. 8A). Conditioned medium (CM) and lysates were obtained after 48 hours and were then detected for the various components of the IL-31 construct by Western Blot.
(FIGS. 8B-E). Detection of the miL-31 part (FIG. 8B), the mCH2-CH3-IgG part (FIG. 8C), the Myc part (FIG. 8D) and the His part (FIG. 8E) using the Goat-a-Rat, G-a-m-IgG, G-a-m-light, G-a-m-light antibodies respectively. Coomassie Brilliant Blue (CBB) stain of 20 mg purified hIL-31-IgG and mIL-31-IgG is shown in FIG. 8F.
(FIGS. 8G-H) The protein IL-31-IgG (both human and mouse) which was generated and purified has been tested for its stability in peripheral blood of mice. C57B16 mice were injected with 30 µg of the indicated IL-31 proteins. Blood was drawn by retro-orbital sinus at different time points, and plasma was separated. Plasma (2 µl) was used to detect the various IL-31 proteins using anti-His-HRP conjugated antibody by Western Blot.
Figures 8G, 8H:
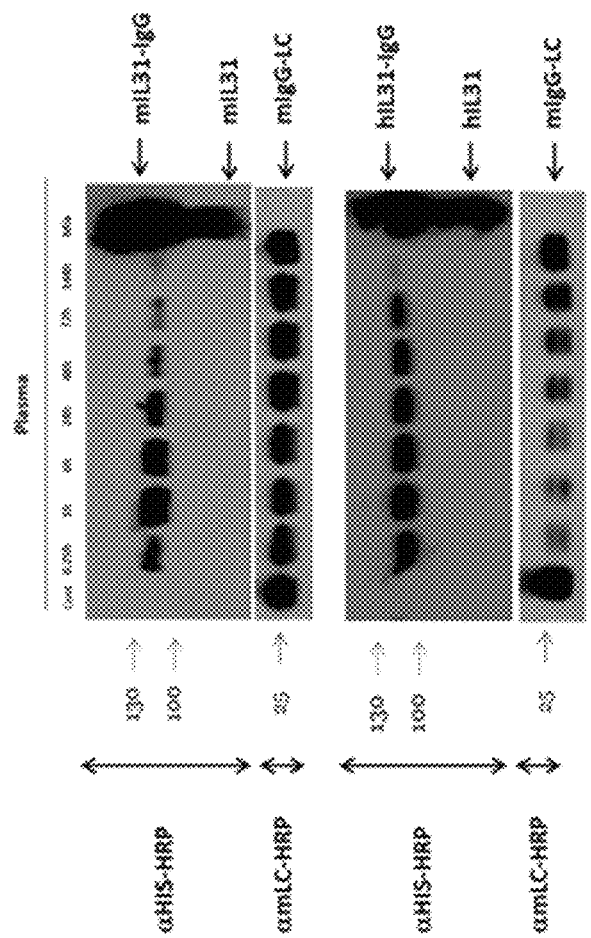

The IL-31-IgG protein stabilization was tested by injecting C57B16 mice 30 μg of the indicated IL-31 proteins (both human and mice). Blood was drawn by retro-orbital sinus at different time points, and plasma was separated. Plasma (2 μl) was used to detect the various IL-31 proteins using anti-His HRP conjugated antibody by Western Blot. It is further noted that FIGS. 8A-H show that IL-31-IgG is stabilized for at least 72 hours in peripheral blood. 293T cells were transfected with the IL-31-Ig construct (FIG. 8A). Conditioned medium (CM) and lysates were obtained after 48 hours and were then detected for the various components of the IL-31 construct by Western Blot. (FIGS. 8B-E). Detection of the miL-31 part (FIG. 8B), the mCH2-CH3-IgG part (FIG. 8C), the Myc part (FIG. 8D) and the His part (FIG. 8E) using the Goat-a-Rat, G-a-m-IgG, G-a-m-light, G-a-m-light antibodies, respectively. Coomassie Brilliant Blue (CBB) (stain of 20 mg purified hIL-31-IgG and mIL-31-IgG is shown in FIG. 8F. The protein IL-31-IgG (both human and mouse), which was generated and purified, has been tested for its stability in peripheral blood of mice. C57B16 mice were injected with 30 μg of the indicated IL-31 proteins. Blood was drawn by retro-orbital sinus at different time points, and plasma was separated. Plasma (2 μl) was used to detect the various IL-31 proteins using anti-His HRP conjugated antibody by Western Blot. (FIG. 8G) 30 μg mIL31-IgG Vs. 200 μg mIL31. (FIG. 8H) 30 μg hIL31-IgG Vs. 200 μg hIL31. hIL-31-PEG represents purified IL-31 protein following PEGylation. FIGS. 8G-H represent the pharmacokinetics of IL31-IgG in the peripheral blood of mice. It shows that while IL-31 is in its native form, it is cleared from the system within 15 min, IL31-IgG is stably present in peripheral blood for the first 72 hours.

Example 8

IL-31 Directly Inhibits Angiogenesis

IL-31 directly inhibits angiogenesis as assessed by tube forming assay:

Human umbilical vascular endothelial cells (HUVECs) were seeded in Matrigel-coated 48-well tissue culture plates (4×104 cells/well) and incubated in 20% FBS M-199 medium. Wells were cultured with 100 ng/ml recombinant human IL-31 or 10 ug/ml human IL-31-IgG. The cells were cultured and phase-contrast images of microvessel tubes were captured after 200 min at 100× magnification using the Leica CTR 6000 (Leica Microsystems). The images were analyzed using ImageJ software and quantified by counting the number of HUVEC junctions (bifurcations) per field.

Figure 9B:
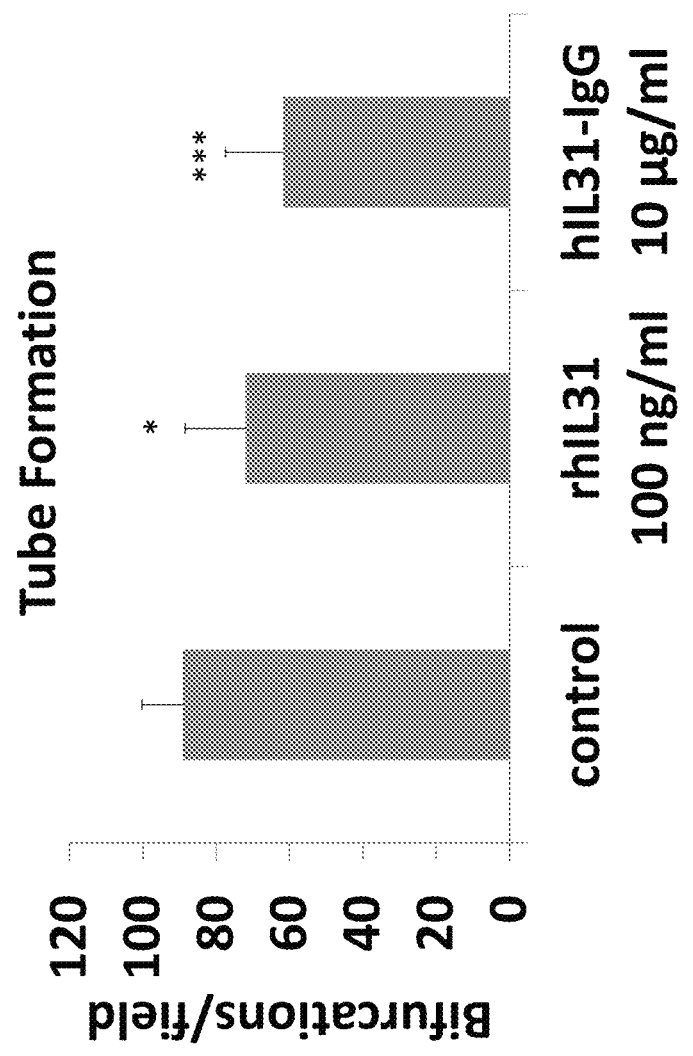
FIGS. 9 (A and B): human umbilical vascular endothelial cells (HUVECs) were seeded in Matrigel-coated 48-well tissue culture plates ($4 \times 10^4$ cells/well) and incubated in 20% FBS M-199 medium. Wells were cultured with 100 ng/ml recombinant human IL-31 or 10 ug/ml human IL-31-IgG. The cells were cultured and phase-contrast images of microvessel tubes were captured after 200 min at 100× magnification using the Leica CTR 6000 (Leica Microsystems). The images were analyzed using ImageJ software and quantified by counting the number of HUVEC junctions (bifurcations) per field.
FIG. 9A shows representative images of tube forming of HUVECs in the presence of 100 ng/ml recombinant human IL-31 (rhIL31) or 10 µg/ml IL-31-IgG are provided 200 min time-point. The number of bifurcations per field were quantified and presented. *, $p<0.05$; ***, $p<0.001$ as shown in FIG. 9B.

FIG. 9A shows representative images of tube forming of HUVECs in the presence of 100 ng/ml recombinant human IL-31 (rhIL31) or 10 μg/ml IL-31-IgG are provided 200 min time-point. The number of bifurcations per field were quantified and presented. *, $p<0.05$; ***, $p<0.001$ as shown in FIG. 9B. As can be seen, IL31 or IL31IgG significantly inhibits tube forming.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating cancer and/or preventing or reducing metastasis of a tumor in a subject comprising the step of administering a composition comprising a peptide comprising amino acids 24-164 of the IL-31 sequence as set forth in SEQ ID NO: 1 to the subject, wherein the cancer or tumor is angiogenesis-dependent and wherein the peptide is not a fused protein, thereby treating cancer and/or reducing or preventing metastasis.

2. The method of claim 1, wherein the cancer is selected from the group consisting of: brain cancer, oropharyngeal cancer, nasopharyngeal cancer, renal cancer, biliary cancer, prostatic cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer and skin cancer.

3. The method of claim 1, wherein the cancer is a hematological malignancy selected from the group consisting of: multiple myeloma, acute lymphocytic leukemia (ALL), acute myeloid leukemia (AML), chronic lymphoblastic leukemia, chronic myeloid leukemia (CML), and mesothelioma.

4. The method of claim 1, wherein the cancer or tumor comprises an IL-31 receptor expressing tumor.

5. The method of claim 1, wherein the cancer comprises a carcinoma.

6. The method of claim 1, wherein the angiogenesis-dependent cancer comprises a solid tumor, a blood-borne tumor, or a tumor metastasis.

7. The method of claim 6, wherein the blood-borne tumor comprises leukemia.

8. The method of claim 1, wherein one or more supporting cells in the tumor microenvironment of said subject express IL-31 receptor.

9. The method of claim 8, wherein said supporting cells comprise endothelial cells, epithelial cells, immune cells, or a combination thereof.

10. The method of claim 9, wherein said immune cells comprise macrophages.

11. The method of claim 1, wherein said peptide consists of amino acids 24-164.

12. A method for treating cancer and/or preventing or reducing metastasis of a tumor in a subject comprising the step of administering a composition comprising a fused protein consisting essentially of a peptide comprising amino acids 24-164 of IL-31 as set forth in SEQ ID NO: 1 and an immunoglobulin heavy chain to the subject, wherein the cancer or tumor is angiogenesis-dependent, thereby treating cancer and/or reducing or preventing metastasis.

13. The method of claim 12, wherein said cancer is selected from the group consisting of brain cancer, oropharyngeal cancer, nasopharyngeal cancer, renal cancer, biliary cancer, prostatic cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer and skin cancer.

14. The method of claim 12, wherein said angiogenesis-dependent cancer comprises a solid tumor, a blood-borne tumor, or a tumor metastasis.

15. The method of claim 14, wherein said blood-borne tumor comprises leukemia.

16. The method of claim 12, wherein said cancer is a hematological malignancy selected from the group consisting of multiple myeloma, acute lymphocytic leukemia (ALL), acute myeloid leukemia (AML), chronic lymphoblastic leukemia, chronic myeloid leukemia (CML), or mesothelioma.

17. The method of claim 12, wherein said cancer comprises a carcinoma.

\* \* \* \* \*

SEQUENCE LISTING

<160> NUMBER OF SEQ ID NOS: 12

<210> SEQ ID NO 1
<211> LENGTH: 164
<212> TYPE: PRT
<213> ORGANISM: Homo sapiens

<400> SEQUENCE: 1

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Val Gln Lys Ile Val Glu Glu Leu Gln Ser Leu
        35                  40                  45

Ser Lys Met Leu Leu Lys Asp Val Glu Glu Glu Lys Gly Val Leu Val
50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 2
<211> LENGTH: 495
<212> TYPE: DNA
<213> ORGANISM: Homo sapiens

<400> SEQUENCE: 2
atggcctctc actcaggccc ctcgacgtct gtgctctttc tgttctgctg cctgggaggc      60
tggctggcct cccacacgtt gcccgtccgt ttactacgac caagtgatga tgtacagaaa     120
atagtcgagg aattacagtc cctctcgaag atgcttttga agatgtggag gaagagaag     180 ggcgtgctcg tgtcccagaa ttacacgctg ccgtgtctca gccctgacgc ccagccgcca     240
aacaacatcc acagcccagc catccgggca tatctcaaga caatcagaca gctagacaac     300
aaatctgtta ttgatgagat catagagcac ctcgacaaac tcatatttca agatgcacca     360
gaaacaaaca tttctgtgcc aacagacacc catgaatgta acgcttcat cctgactatt     420 tctcaacagt tttcagagtg catggacctc gcactaaaat cattgacctc tggagcccaa     480
caggccacca cttaa                                                      495

<210> SEQ ID NO 3
<211> LENGTH: 492
<212> TYPE: DNA
<213> ORGANISM: Mus musculus

<400> SEQUENCE: 3
atgatcttcc acacaggaac aacgaagcct accctggtgc tgctttgctg tataggaacc      60
tggctggcca cctgcagctt gtccttcggt gccccaatat cgaaggaaga cttaagaact     120

| | |
|---|---|
| acaattgacc tcttgaaaca agagtctcag gatctttata caactatag cataaagcag | 180 |
| gcatctggga tgtcagcaga cgaatcaata cagctgccgt gtttcagcct ggaccgggaa | 240 |
| gcattaacca acatctcggt catcatagca catctggaga aagtcaaagt gttgagcgag | 300 |
| aacacagtag atacttcttg ggtgataaga tggctaacaa acatcagctg tttcaaccca | 360 |
| ctgaatttaa acatttctgt gcctggaaat actgatgaat cctatgattg taaagtgttc | 420 |
| gtgcttacgg ttttaaagca gttctcaaac tgcatggcag aactgcaggc taaggacaat | 480 |
| actacatgct ga | 492 |

<210> SEQ ID NO 4
<211> LENGTH: 681
<212> TYPE: DNA
<213> ORGANISM: Mus musculus

<400> SEQUENCE: 4

| | |
|---|---|
| gtgcccaggg attgtggttg taagccttgc atatgtacag tcccagaagt atcatctgtc | 60 |
| ttcatcttcc ccccaaagcc caaggatgtg ctcaccatta ctctgactcc taaggtcacg | 120 |
| tgtgttgtgg tagacatcag caaggatgat cccgaggtcc agttcagctg gtttgtagat | 180 |
| gatgtggagg tgcacacagc tcagacgcaa ccccgggagg agcagttcaa cagcactttc | 240 |
| cgctcagtca gtgaacttcc catcatgcac caggactggc tcaatggcaa ggagttcaaa | 300 |
| tgcagggtca acagtgcagc tttccctgcc ccatcgaga aaccatctc caaaccaaa | 360 |
| ggcagaccga aggctccaca ggtgtacacc attccacctc caaggagca gatggccaag | 420 |
| gataaagtca gtctgacctg catgataaca gacttcttcc ctgaagacat tactgtggag | 480 |
| tggcagtgga atgggcagcc agcggagaac tacaagaaca ctcagcccat catggacaca | 540 |
| gatggctctt acttcgtcta cagcaagctc aatgtgcaga gagcaactg ggaggcagga | 600 |
| aatactttca cctgctctgt gttacatgag ggcctgcaca ccaccatac tgagaagagc | 660 |
| ctctcccact ctcctggtaa a | 681 |

<210> SEQ ID NO 5
<211> LENGTH: 696
<212> TYPE: DNA
<213> ORGANISM: Homo sapiens

<400> SEQUENCE: 5

| | |
|---|---|
| gagcccaaat cttgtgacaa aactcacaca tgcccaccgt gcccagcacc tgaactcctg | 60 |
| gggggaccgt cagtcttcct cttcccccca aaacccaagg acaccctcat gatctcccgg | 120 |
| acccctgagg tcacatgcgt ggtggtggac gtgagccacg aagaccctga ggtcaagttc | 180 |
| aactggtacg tggacggcgt ggaggtgcat aatgccaaga caaagccgcg ggaggagcag | 240 |
| tacaacagca cgtaccgtgt ggtcagcgtc ctcaccgtcc tgcaccagga ctggctgaat | 300 |
| ggcaaggagt acaagtgcaa ggtctccaac aaagccctcc cagcccccat cgagaaaacc | 360 |
| atctccaaag ccaaagggca gccccgagaa ccacaggtgt acaccctgcc cccatcccgg | 420 |
| gaggagatga ccaagaacca ggtcagcctg acctgcctgg tcaaaggctt ctatcccagc | 480 |
| gacatcgccg tggagtggga gagcaatggg cagccggaga caactacaa gaccacgcct | 540 |
| cccgtgctgg actccgacgg ctccttcttc ctctacagca agctcaccgt ggacaagagc | 600 |
| aggtggcagc aggggaacgt cttctcatgc tccgtgatgc atgaggctct gcacaaccac | 660 |
| tacacgcaga agagcctctc cctgtctccg ggtaaa | 696 |

-continued

```
<210> SEQ ID NO 6
<211> LENGTH: 163
<212> TYPE: PRT
<213> ORGANISM: Mus musculus

<400> SEQUENCE: 6

Met Ile Phe His Thr Gly Thr Thr Lys Pro Thr Leu Val Leu Leu Cys
1               5                   10                  15

Cys Ile Gly Thr Trp Leu Ala Thr Cys Ser Leu Ser Phe Gly Ala Pro
            20                  25                  30

Ile Ser Lys Glu Asp Leu Arg Thr Ile Asp Leu Leu Lys Gln Glu
        35                  40                  45

Ser Gln Asp Leu Tyr Asn Asn Tyr Ser Ile Lys Gln Ala Ser Gly Met
    50                  55                  60

Ser Ala Asp Glu Ser Ile Gln Leu Pro Cys Phe Ser Leu Asp Arg Glu
65                  70                  75                  80

Ala Leu Thr Asn Ile Ser Val Ile Ala His Leu Glu Lys Val Lys
                85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
        115                 120                 125

Gly Asn Thr Asp Glu Ser Tyr Asp Cys Lys Val Phe Val Leu Thr Val
    130                 135                 140

Leu Lys Gln Phe Ser Asn Cys Met Ala Glu Leu Gln Ala Lys Asp Asn
145                 150                 155                 160

Thr Thr Cys

<210> SEQ ID NO 7
<211> LENGTH: 8
<212> TYPE: PRT
<213> ORGANISM: Homo sapiens

<400> SEQUENCE: 7

Gly Pro Leu Gly Ile Ala Gly Gln
1               5

<210> SEQ ID NO 8
<211> LENGTH: 5
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa is epsilon-maleimidocaproic

<400> SEQUENCE: 8

Lys Lys Phe Ala Xaa
1               5

<210> SEQ ID NO 9
<211> LENGTH: 8
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa is D-arginine

<400> SEQUENCE: 9

Lys Gly Ala Ser Xaa Phe Thr Gly
1               5
```

```
<210> SEQ ID NO 10
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa is epsilon-maleimidocaproic

<400> SEQUENCE: 10

Xaa Arg Arg Ser Ser Tyr Tyr Ser Gly
1               5

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
taccgctcga ggtgcccagg gattgtggtt g                               31

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
cgttcgaatt taccaggaga gtggg                                      25
```